US012778788B2

(12) United States Patent
Binding et al.

(10) Patent No.: US 12,778,788 B2
(45) Date of Patent: Nov. 3, 2026

(54) LIQUID CAPTURE DEVICE

(71) Applicant: LUII LIMITED, Cropredy (GB)

(72) Inventors: Keith Binding, Farnborough (GB); Sarah Leather, Farnborough (GB)

(73) Assignee: LUII LIMITED (GB)

( * ) Notice: Subject to any disclaimer, the term of this patent is extended or adjusted under 35 U.S.C. 154(b) by 610 days.

(21) Appl. No.: 18/271,146

(22) PCT Filed: Jan. 7, 2022

(86) PCT No.: PCT/GB2022/050026

§ 371 (c)(1),
(2) Date: Jul. 6, 2023

(87) PCT Pub. No.: WO2022/148965

PCT Pub. Date: Jul. 14, 2022

(65) Prior Publication Data

US 2024/0050264 A1 Feb. 15, 2024

(30) Foreign Application Priority Data

Jan. 8, 2021 (GB) ..................................... 2100266
Nov. 15, 2021 (GB) ..................................... 2116440

(51) Int. Cl.
*A61F 5/455* (2006.01)
*A61F 5/453* (2006.01)

(52) U.S. Cl.
CPC .............. *A61F 5/455* (2013.01); *A61F 5/453* (2013.01)

(58) Field of Classification Search
CPC ........ A61F 5/455; A61F 5/453; A61F 5/4401; A61F 5/4405; A61F 5/451
See application file for complete search history.

(56) References Cited

U.S. PATENT DOCUMENTS 4,707,864 A * 11/1987 Ikematsu ............... A61G 9/006 4/144.3
5,422,076 A 6/1995 Jones
5,571,095 A * 11/1996 Lu .......................... A61G 9/006 600/574
5,871,037 A * 2/1999 Feldt ......................... B65F 1/10 141/390
8,603,056 B1 * 12/2013 Fallis ...................... A61F 5/455 604/318
9,744,068 B2 * 8/2017 Hughes ................... A61F 5/451
10,112,734 B1 * 10/2018 Schrager ................. B65B 67/04
2004/0026578 A1 2/2004 King et al.
2004/0195467 A1 * 10/2004 Passage .............. B65B 67/1255 248/95
2006/0074389 A1 4/2006 Montgomery
2008/0269700 A1 * 10/2008 O'Toole ................ A61F 5/4405 604/332

(Continued)

FOREIGN PATENT DOCUMENTS

CN 101010049 A * 8/2007 ............. A61F 5/453
DE 202010006923 U1 * 8/2010 ........... A61F 5/4556

(Continued)

*Primary Examiner* — Rebecca E Eisenberg
*Assistant Examiner* — Matthew Wrubleski
(74) *Attorney, Agent, or Firm* — The Belles Group, P.C.

(57) ABSTRACT

Provided is a liquid capture device for bodily excreta comprising a collection bag, comprising a collar portion and a bag portion, and a holder adapted to support the collection bag in use.

17 Claims, 21 Drawing Sheets

(56) References Cited

U.S. PATENT DOCUMENTS

| | | | | |
|---|---|---|---|---|
| 2009/0234312 | A1 | 9/2009 | O'Toole et al. | |
| 2011/0270203 | A1* | 11/2011 | Sharpe | A61F 5/451 604/326 |
| 2011/0309209 | A1* | 12/2011 | Muse | B65B 39/007 248/97 |
| 2012/0222208 | A1 | 9/2012 | Jacobson et al. | |
| 2013/0110059 | A1* | 5/2013 | Kossow | A61F 5/455 604/329 |
| 2015/0135423 | A1 | 5/2015 | Sharpe et al. | |
| 2018/0014991 | A1* | 1/2018 | Leon | A61G 9/006 |
| 2018/0177247 | A1 | 6/2018 | Lin et al. | |
| 2018/0296385 | A1 | 10/2018 | Ohler et al. | |

FOREIGN PATENT DOCUMENTS

| | | | | |
|---|---|---|---|---|
| EP | 0555607 | A1 | 8/1993 | |
| EP | 0576754 | A1 * | 1/1994 | A61F 5/445 |
| GB | 2304577 | A | 3/1997 | |
| GB | 2529165 | A | 2/2016 | |
| KR | 200377523 | Y1 * | 3/2005 | A47K 11/00 |
| KR | 20180096970 | A | 8/2018 | |
| WO | 2013131109 | A1 | 9/2013 | |
| WO | 2019206941 | A1 | 10/2019 | |

* cited by examiner

LIQUID CAPTURE DEVICE

CROSS-REFERENCE TO RELATED PATENT APPLICATIONS

The present application is a U.S. national stage application under 35 U.S.C. § 371 of PCT Application No. PCT/GB2022/050026, filed Jan. 7, 2022, which claims priority to United Kingdom Patent Application No. 2100266.2, filed Jan. 8, 2021, and United Kingdom Patent Application No. 2116440.5, filed Nov. 15, 2021. The disclosures of the aforementioned priority applications are incorporated herein by reference in their entireties.

TECHNICAL FIELD

The present invention relates generally to a liquid capture device for bodily excreta, in particular urine, and more specifically to a self-contained liquid capture device for bodily fluids. Also described is a blank for forming a collar adapted to support a neck portion of a collection bag, and a method of assembling a collar adapted to support a neck portion of a collection bag.

BACKGROUND

A range of devices exist which are designed to reduce spillage of bodily excreta and/or to direct the flow of excreta away from the user. They fall in to three main categories: i) Non-invasive worn absorbent devices, such as nappies, incontinence pads and pants, which are typically in prolonged contact with the skin, ii) Non-invasive non-worn devices such as bedpans and handheld urinals that are in transitory contact with the skin, and iii) Invasive devices, such as urinary catheters, that are typically in place for long periods of time.

Non-invasive worn absorbent devices may be particularly designed to cater for infants or incontinent adults. However, such devices suffer from a number of problems. For instance, incontinence pads and pants bulk up as the absorbent polymers from which they are made absorb fluid; often suffer from leakage when the absorbent polymers reach saturation; and can cause skin lesions or rashes and contribute to pressure ulcers, which may lead to hospitalisation, due to prolonged contact with the body.

Non-invasive non-worn devices typically cater to users who are continent but who nonetheless are unable to use, or have difficulty in using, conventional toilet facilities. For instance, users who have restricted physical mobility, or in circumstances in which a user is confined to bed or a wheelchair or is immobilised for medical reasons such as illness, injury or childbirth. Such devices include bedpans and multi-use urine bottles. These devices can be difficult to use, require cleaning, and there is a likelihood of urine spillage on skin, clothing and bed linen. In particular, it may be difficult for wheelchair users and women to use these devices, especially when seated, if at all or without getting wet. The closures used on multi-use urine bottles may be difficult to open and close, in particular for those with ataxia, for example, some stroke sufferers. Bedpans may be difficult or uncomfortable to use; may be bulky; require cleaning; and are prone to spillage. Further, bedpans can be noisy to use. This may be particularly undesirable for users in a general ward environment.

This class of device also caters for people who require an ad hoc urine capture facility or who have limited access to sanitary toilet facilities. In particular, people can experience difficulties locating acceptable toilet facilities whilst travelling, camping, attending outdoor events, participating in outdoor activities and sports, and generally when out and about. In such situations a person may be forced to urinate in a standing or squatting position. Again, this is especially difficult for women, as the female anatomy does not allow a woman to control the direction of flow of discharging urine. Urine bottles, such as Uriwell®, fall into this class of device, as well as funnel devices, such as the SheWee® funnel, and disposable urine bags, such as TravelJohn® and Peebol®. Again, concerns with urine bottles include that they are difficult to use for people with restricted physical mobility, manual dexterity and/or visual impairment. For example, opening and closing the lid, emptying, and cleaning them thoroughly may be difficult. In addition, they are bulky to carry around and prone to leaking. Whilst funnel devices, such as the SheWee® funnel, are relatively easy to use, they do not capture fluids and require cleaning after use. Disadvantages associated with disposable urine bags include that they tend to be difficult or impossible to use in a seated position; are prone to leakage; are utilitarian in appearance; and tend to be difficult to seal after use for those with reduced dexterity.

Invasive devices such as catheters may be difficult to insert and remove, particularly for those with restricted mobility or dexterity, sometimes do not work, and are associated with much increased incidence of urinary tract infections.

Due to the above-described disadvantages infirm persons are often unable to independently manage their toileting, and thus require assistance from a carer. This often has significant adverse effects on their health, wellbeing, and quality of life, and on that of their carers.

Worn absorbent devices and invasive devices are sometimes supplied by healthcare providers to continent users for the operational convenience of the former, rather than the clinical need of the latter.

There therefore exists a need to overcome one or more of the aforementioned disadvantages.

SUMMARY OF THE INVENTION

The present invention is a liquid capture device for bodily excreta comprising a collection bag, comprising a collar portion and a bag portion; and a holder adapted to support the collection bag in use. The holder has an opening, and wherein the collar portion of the collection bag is adapted to conform to the holder, and the bag portion of the collection bag is adapted to receive and store fluid, wherein the collection bag is removably or permanently attached to the holder. The attachment means comprises at least one protrusion on an external surface of the holder and at least one complementary cut out in the collar of the collection bag, preferably, wherein the attachment means comprises at least two protrusions on the external surface of opposite sides of the holder and at least two complementary cut-outs in opposite sides of the collar of the collection bag.

Accordingly, a device is provided which is able to capture bodily fluids and is easy to use for those with reduced manual dexterity and/or visual impairment.

It is possible for cut outs in the collection bag to rest on top of (or “hook over”) the protrusions. In some embodiments, the protrusions additionally comprise recesses adapted to securely attach the collection bag to the holder. The protrusions may have any shape. In some embodiments, the top of the protrusions is a flat surface. In some embodiments, the protrusions have a concaved or convex surface.

In a preferred embodiment, the protrusions have a horizontal upper face and at least two side faces. This prevents the collection bag being able to move either fore or aft or up and off the protrusions, thus providing a secure and reliable fixing of the collection bag to the holder while enabling easy attachment and detachment of the collection bag to the holder. This provides the user, particularly those with impaired manual dexterity, with both confidence in the reliability of the device and convenience in use.

In some embodiments, the holder may comprise an upper part and a lower part wherein the upper part is attached to the lower part, and the upper part is additionally secured to the lower part by way of a securing means. The upper part of the holder matches the profile of the lower part of the holder, such that when the hinge is closed a seal is formed between the upper and the lower part. The collection bag may be held in place by trapping the bag between the upper and lower part. The upper and lower part may be closed by way of a securing means on the upper and lower part.

The upper part may be attached to the lower part by a hinge, and a means of securing the lower part to the upper part. The means of securing the lower part to the attachment means may be one or more complementary male and female snaps on the upper and lower part; one or more complementary hook and eye fasteners on the upper and lower part; one or more toggles on the upper or lower part and one or more complementary cut outs in the upper or lower part; one or more buttons on the upper or lower part and one or more complementary cut outs in the upper or lower part; complementary hook and loop (Velcro™) tape on the upper and lower part; one or more complementary magnetic strips on the upper and lower part; one or more adhesive strips on the upper and lower part; or combinations thereof.

In some embodiments, the holder of the liquid capture device is shaped such that it conforms to the human pubic region. For example, the holder may have a generally oval shape with raised sides. The sides may be textured to enable a user to easily hold the holder during use. In some embodiments the sides are deep enough to enable the user to easily hold the holder, but small enough to enable discreet storage of the device and ease of use. For example, in some embodiments the holder may be from 1 cm to 5 cm deep, preferably from 2 cm to 5 cm deep. The longitudinal length of the holder may be from 5 cm to 20 cm long, preferably from 8 cm to 12 cm long. The width of the holder may be from 4 cm to 8 cm wide, preferably from 4 cm to 6 cm wide.

In some embodiments, the liquid capture device further comprises an insert adapted to fix to the holder. The inset may clip onto the top of the holder. The inset may be shaped such that it conforms to the human public region, or to human genitalia. For example, the inset could have a circular aperture suitable for conforming to a penis. In some embodiments, the aperture could be modified for increased comfort by the inclusion of padding. In some embodiments, the inset may be 3D printed to provide a personalised fit to the user.

In preferred embodiments, the holder or inset is shaped such that it forms a seal when positioned on the human pubic region. Preferably, the holder is shaped to conform to the female pubic region. In some embodiments, a first part of the holder is shaped to conform to an upper part of the vulva and a second part of the holder is shaped to conform to the area underneath a lower part of the vulva towards and beyond the perineum. This enables the device to be used by females in a seated position.

The liquid capture device is also suitable to be used to capture bodily excreta, other than urine, such as vomit or faeces. In these cases, the holder may be shaped to conform to the part of the body from which said other bodily fluid is excreted. For instance, in the case of a liquid capture device for vomit, the holder may be shaped to conform to the human face, and optionally form a seal therewith.

In some embodiments, the holder further comprises an angled arm at one end. The arm may be at an acute or right angle to a longitudinal axis of the bag. For example, the arm may be at an angle of 15 degrees to 90 degrees. In some embodiments, the arm is shaped to provide a means for easy holding of the device. For example, the arm may be shaped to conform to the human hand or be a gently curved shape. In some embodiments, the arm has a length between 5 cm and 15 cm, preferably between 5 cm and 10 cm. The arm may have a circumference of between 9 cm and 16 cm.

The inclusion of an angled arm on the holder of the device means that the device is easier to hold and use for people with limited mobility, dexterity and/or vision. The angled arm also provides an indication of the orientation of the device next to the body, which in turn improves the seal between the holder and the user's body when in use. The angled arm provides leverage enabling those with poor musculature and/or manual dexterity to create a leakproof seal between the rim of the holder and the user's body when in use by applying only minimal pressure to the arm.

The angled arm enables the holder to be held upside down between the user's knees, enabling the collection bag to be attached single-handed, thus enabling those with poor upper limb coordination, for example, stroke patients, to use the device without assistance.

The angled arm may have a textured or rough surface to allow a user to easily hold the device. For example, the textured surface may be a ridged surface, comprise a number of raised shapes, or a number of indentations. In some embodiments, the angled arm may have a coating configured to improve grip. In some embodiments, the angled arm may have depressions that correspond with the palm and/or fingers of a human hand.

The angled arm may be separated from the aperture part of the holder by a bridge section. The bridge section is preferably 1 to 7 cm wide. The inclusion of a bridge section enables those with larger hands, or reduced dexterity or strength to easily hold the handle using different grips in multiple orientations.

The collection bag may be attached to the holder of the liquid capture device. The collection bag may be removably or permanently attached to the holder. When the collection bag is removably attached to the holder, it is envisaged that the holder will be reused and the collection bag will be disposed of after use. That is, the collection bag can be safely disposed of without the need for the user to clean or otherwise sterilise the inside of the bag. Alternatively, the collection bag may be permanently attached to the holder. In this embodiment, it is envisaged that the entire liquid capture device will be disposed of after use. In the embodiment where the collection bag is removably attached to the holder, the holder may be made of any material that can be washed, cleaned, sterilised or disinfected so that it can be reused.

In some embodiments, the collection bag may be removably attached to the holder by means of friction alone. In this case, the size of the collar of the collection bag and the outer surface of the holder are similar. The internal and/or external surface of the collar of the collection bag and/or the internal and external surfaces of the holder may be textured or have a rough surface to improve friction.

In some embodiments, the collar of the collection bag is made of a resilient or pliable material. In such embodiments, the collection bag can be attached to the holder by applying light pressure to the ends of the collar of the collection bag, resulting in slight deformation of the collar. The slight deformation allows for the cut outs in the collar to fit over the protrusions in the holder and, upon pressure on the ends of the collar being released, for the collar to grip the protrusions firmly such that the collection bag is securely attached to the collar. The collection bag can be easily released from the holder by applying light pressure to the ends of the collar of the collection bag resulting in slight deformation of the collar. The slight deformation of the collar allows for the cut outs in the collar to be released from the protrusions in the holder allowing the collection bag to be removed from the holder and/or allowing the attachment of a new collection bag to the holder. This mechanism allows for the easy removal and attachment of collection bags to the holder. The removal and attachment can be performed with only one hand and requires only two digits. A further advantage of this attachment mechanism is that the user does not need to place their hands inside the collection bag or onto the inner surface of the holder which may be unhygienic.

In some embodiments, the holder is made of a resilient or pliable material. In such embodiments, the collection bag can be released from the holder by applying minimal pressure using the digits of one hand to the ends of the holder resulting in slight deformation of the holder. The slight deformation of the holder allows for the cut outs in the collar of the collection bag to be released from the protrusions in the holder, allowing the collection bag to be removed from the holder and/or allowing the attachment of a new collection bag to the holder. This mechanism allows for the easy attachment and removal of collection bags from the holder, in particular by users with poor manual dexterity (such as arthritis sufferers) or ataxia (for example, stroke patients). As above, a further advantage of this attachment mechanism is that the user does not need to place their hands inside the collection bag or onto the inner surface of the holder which may be unhygienic.

In some embodiments, the collection bag may be secured to the holder by trapping the collection bag between an upper and a lower part of the holder.

In some embodiments, the removable attachment means may be a draw string mechanism. In this embodiment the collar of the collection bag further comprises a draw string that can be tightened when placed over the holder. This attachment means may be used in combination with the friction attachment means described above and/or may be used in combination with the complementary protrusions and cut outs also described above.

In some embodiments, the collection bag is configured to be attached to the internal surface of the holder. In some embodiments, the collection bag can be placed through the opening of the holder and folded over the top of the holder. In this embodiment, the collection bag may be further secured to the holder by way of a draw string that tightens the collection bag over the holder.

In other embodiments, the collection bag may be secured to the internal or external surface of the holder by any of the attachment means mentioned herein. For example, in a preferred embodiment, the collection bag may be secured to the internal surface of the holder by way of complementary protrusions and cut outs as described above.

In some embodiments, the attachment means described above may be used in combination with any one of the following attachment means. Alternatively, the following attachment means may be used in isolation. Suitable attachment means include one or more complementary male and female snaps on the holder and the collar of the collection bag; one or more complementary hook and eye fasteners on the holder and the collar of the collection bag; one or more toggles on the holder and one or more complementary cut outs in the collar of the collection bag; one or more buttons on the holder and one or more complementary cut outs in the collar of the collection bag; complementary hoop-and-loop fastener tape, like Velcro™ tape, on the holder and the collar of the collection bag; one or more complementary magnetic strips on the holder and on the collar of the collection bag; one or more adhesive strips on the holder and/or collar of the collection bag; one or more friction rings on the holder and/or the bag; or any combination thereof.

As mentioned above, in some embodiments, the holder is made of a resilient or pliable material. Preferably, the holder is made from an elastic material that can be reversibly deformed to aid in the attachment and detachment of the collection bag and aid in forming a seal with the user's body when in use. Examples of suitable materials include, but are not limited to, polysiloxane, polymers, composites, metal alloys, and biomaterials.

In some embodiments, antimicrobial materials are incorporated into the holder and/or collection bag. Such materials are well known to the skilled person. Examples include, but are not limited to, copper, brass, silver, cupronickel, organosilanes, and specially designed polymers.

In some embodiments, the holder material will be biodegradable. "Biodegradable" is used here to mean that the material is completely decomposed by bacteria or other living organisms under atmospheric conditions in under 5 years. Accordingly, pollution caused as a result of discarded devices may be reduced.

In some embodiments, the holder material will be reusable. This reduces waste. In such embodiments, the device may comprise a long-lasting material. In this case, "long-lasting" refers to any material suitable for a device that can be used more than once. For example, the material should be such that it can be washed, sterilised, and/or disinfected.

In some embodiments, it is preferred that the holder material is non-elastic and/or that the material of the holder is biodegradable. Suitable materials include, but are not limited to, cellulose-based materials and lignin-based materials. For example, bamboo fibers, cork, mycelium, seaweed, and hemp.

The collection bag may be made of any suitable material appropriate for collecting and storing liquid. Examples of suitable materials may include plastic, coated paper, coated fabric, or foil. In some embodiments, the collection bag may be made of a combination of materials.

In some embodiments, the collection bag may further comprise a sealing mechanism. The sealing mechanism may be useful to seal the collection bag after it has been detached from the holder. This enables the user to seal the bag after use. In preferred embodiments the seal is a water-proof seal so that neither fluids nor solids can leak out of the bag after it is sealed. Suitable sealing mechanisms include, but are not limited to, a ziplock, a roll top, one or more clips, drawstring, interlocking strips, adhesive, or combinations thereof.

To aid in the use of the device, in some embodiments, an inner surface of the holder may comprise one or both of a fluid channel and a raised element. The fluid channel and/or raised element are configured to direct liquid entering the holder towards the opening of the holder and into the collection bag when in use. The raised element and/or channel may also be used to form a seal to prevent the flow of fluid beyond the perineum towards the anus. This speeds up the drainage of the liquid from the holder into the collection bag, thus improving comfort for the user by keeping them dry.

In some embodiments the holder has a front end and a back end. The front end is directed towards the anus when in use. In some embodiments, the holder may have a spoonbill shape or any other shape that enables users, in particular larger persons, to place the device so as to create a leakproof seal between the device and the user's body.

In some embodiments, the holder may comprise a concave portion which forms a cavity into which most of the liquid is initially received during use, and further wherein the depth and shape of that concave portion is configured to reduce a flow velocity of liquid impinging thereon. This helps to reduce splashback and thus helps to keep the user dry. In some embodiments, the holder has a hydrophobic or high-resolution internal surface. This will maximise flow of fluid into the bag and minimise the likelihood of residual fluid remaining on the upper surfaces of the holder. The surface of the holder can therefore be easily cleaned without the need for harsh cleaning methods. This improves the ease of use of the device.

In some embodiments, the liquid capture device comprises one or more absorbent materials. Suitable absorbent materials include cotton, napkins, sponge, anhydrous calcium chloride, soda lime, aliochronic silica gel, activated carbon, absorbent or superabsorbent polymers (SAP) or absorbent or super absorbent fibers (SAF). Preferably, the absorbent material is provided inside the collection bag, optionally attached to the inside of the collection bag. Preferably the absorbent material comprises one or more superabsorbent materials. Superabsorbent materials are able to hold and retain extremely large volumes of water and aqueous solutions inside, relative to their own mass. Examples of superabsorbent materials are superabsorbent fibers and polymers. "Superabsorbent polymer" (SAP) is used here to mean a water absorbing polymer which is able to absorb at least 100 times its own mass in deionised water. The SAP will absorb water in the urine and form a hydrogel in which water is held within a solid structure. Accordingly, water absorbed by the SAP is unable to flow out of the bag, reducing leakage of the bag's contents. A superabsorbent fiber (SAF) is produced by mixing a superabsorbent material with a hydrophobic/hydrophilic material, or by fiber spinning a superabsorbent polymer with dry or wet spinning technology. Preferably the absorbent material comprises one or more superabsorbent polymers. Examples of SAPs that may be used include polyacrylates, polyacrylate/polyacrylamide copolymers, starch-acrylonitrile co-polymers, and protein/poly(acrylic acid) superabsorbent polymers. The absorbent material is preferably biodegradable.

In some embodiments, the SAP or SAF are contained within a sachet attached to or contained within the liquid capture device. Preferably the sachet is soluble in liquid. In other embodiments, the SAP may be in the form of free-flowing granules loose in the collection bag. Alternatively, the SAP may be attached to an internal surface of the collection bag for example, by spray coating the internal surface of the collection bag or by applying it in a hot-melt formulation. The SAF may also be adhered to the inside surface of the bag or enclosed in the bag using any appropriate means.

In some embodiments, at least two different superabsorbent polymers may be used. In some embodiments the at least two different superabsorbent polymers are attached to the inside of the bag. The different superabsorbent polymers comprising a first polymer attached to an upper region of the bag and a second polymer attached to a different part of the bag, for example a bottom part of the bag. In these embodiments, the second polymer has a higher absorption rate than the first polymer. Here, "different" superabsorbent polymers include SAPs having polymer chains with different chemical compositions, as well as SAPs having polymer chains with the same chemical compositions, but with different degrees of crosslinking between the polymer chains.

Accordingly, the second polymer with the higher absorption rate can capture the vast majority of liquid, whilst the first polymer in the upper region can capture residual fluid. The lower absorption rate avoids the first polymer from expanding in mid-flow and impeding or blocking the flow of liquid into the bag.

Optionally, the collection bag may also comprise an odour absorber, anti-microbial agents, fragrances, colouring agents and/or adhesives. These additional agents may be mixed with the absorbent materials or may be provided separately inside or on the surface of the collection bag.

In some embodiments, the collection bag further comprises a gusset at a bottom of the bag. The gusset may be conformed to enable the collection bag to stand without further support. This improves the usability of the device so as the user may place the bag onto a surface without spilling any liquid whilst they attend to other matters.

In some embodiments, the collection bag may be further angled from the holder to aid the flow of liquid into a bottom of the collection bag by gravity when in use. This will increase the speed at which liquid drains out of the holder and into the collection bag, ensuring that the user stays dry and reducing the possibility of liquid leaking from the device whilst in use.

In some embodiments, the collection bag is die cut to ensure size compatibility with the collar.

Optionally, the bag may comprise at least one of a thermochromic ink and/or dye and a hydrochromic ink and/or dye. The thermochromic ink and/or dye may be applied to either of the inner and outer surfaces of the bag. The hydrochromic ink and/or dye may be applied to the inner surface of the bag. The colour change of the thermochromic ink and/or dye will be activated by the temperature of the urine in the bag, optionally allowing a design to become visible. On the other hand, the hydrochromic ink and/or dye will be activated to change colour upon coming into contact with water in the bodily fluid.

Examples of thermochromic inks that may be used include thermochromic liquid crystals (TLC) and leuco dyes. The thermochromic ink is activated by the temperature of the user's urine when it enters the collection bag, causing the design to change colour. The colour change effected by the thermochromic ink may be a change from a first colour to a second colour, the first and second colours being different; or, alternatively, the colour change may be from a first colour to colourless or vice versa. Accordingly, for colour changes involving a change from or to a colourless design, the design is caused to be revealed or to disappear, respectively. Three methods (method A, method B and method C) are provided below for manufacturing a device according to this embodiment.

Method A

Method A involves printing the bag in a conventional, non-colour changing ink, and incorporating the design in the print in negative. A hydrochromic dye is then added to the permeable sachet or otherwise incorporated into the SAP or SAF, such that upon contact with urine, the SAP or SAF will expand and change colour. As the expanded gel comes in to contact with the face of the bag, the design will appear to change from clear/translucent to coloured.

Method B

Method B involves printing the bag in a conventional, non-colour changing ink, and incorporating the design in the print in negative. An inside surface of the bag is then printed with hydrochromic ink in the region of the negative design. In some embodiments, Method B may involve selecting a hydrochromic ink which changes colour from a first colour which is the same as the colour of the conventional ink used to print the design in negative. Accordingly, the design is revealed by changing colour to a second colour which is different from the colour of the rest of the bag, or by becoming colourless.

Method C

Method C involves printing the bag in conventional, non-colour changing ink, and incorporating the design in the print in negative. A hydrochromic dye is then added to the permeable sachet or otherwise incorporated into the SAP or SAF. A hydrochromic or thermochromic ink, which changes colour from a first colour to colourless, is then applied over the negative design on an inside or outside surface of the collection bag. Accordingly, when liquid enters the collection bag, the negative design will change colour. As more liquid is added to the bag, the SAP or SAF will expand and change colour. As the expanded gel comes in to contact with the face of the bag, the design will change to the colour of the dye-infused SAP or SAF.

The colour change effect acts as both a stimulus to, and reward for, urinating into the device. As such, this embodiment may have particular advantages in encouraging toddlers and young children to recognise when they need to urinate and respond by actively seeking to use the device. The device may also offer similar benefits for those with impaired cognitive function including, but not limited to, dementia sufferers who retain some degree of cognition and voluntary control. In the latter case, the colour change effect may remind the user of the purpose of the device.

The present invention also provides a method of capturing bodily fluids comprising: providing the liquid capture device defined above.

In some embodiments, the present invention also provides a blank for forming a collar adapted to support a neck portion of a bag, preferably, the collection bag described above. The blank comprising: a first portion; a second portion configured to be folded over to overlie the first portion; a fold line located between the first and second portion, wherein, when the second portion overlies the first portion, and the fold line is compressed, an aperture is defined between the first and second portions. The aperture creates a path through the collar such that material can pass into the bag through the neck portion. As the collar is formed from a blank, a sheet material can be used such as card, for increased environmental sustainability.

In some embodiments, the fold line comprises a through cut that passes through the depth of the blank, wherein the through cut expands in a direction perpendicular to the fold line as the fold line is compressed, to define the aperture.

In some embodiments, the fold line comprises a frangible portion, the frangible portion forming the through cut as the fold line is compressed, optionally wherein the frangible portion is a perforated line. This means that the first and second portions of the blank do not separate until the fold line is compressed, which provides a means of securely containing solid and semi-solid materials within the collection bag until the said aperture is formed through compression of the fold line and which aids in transport and storage of the contents of the said collection bag.

In some embodiments, the first portion comprises a first panel and a second panel, and the second portion comprises a first panel and a second panel, wherein when the second portion overlies the first portion, the second panel of the second portion is configured to be folded to overlie the first panel of the second portion. This arrangement provides extra rigidity to the collar.

In some embodiments, an underside of the first panel of the first portion and an underside of the first panel of the second portion are configured to engage an internal surface of the neck portion of the bag. This enables part of the collar to locate within the neck portion of the bag. Preferably, an underside of the second panel of the first portion and an underside of the second panel of the second portion are configured to engage an external surface of the neck portion of the bag. The second panel of the first portion and the second panel of the second portion can be easily fixed to the neck portion of the collection bag.

In some embodiments, the blank further comprises first and second side tabs configured to extend between the first portion and the second portion when the collar is formed. The side tabs provide further rigidity to the collar. In a preferred embodiment, the first and second side tabs project from the first panel of the first portion and are configured to locate between the first and second panels of the second portion. This provides a more aesthetic appearance and can be fixed to both the bag and the second portion, if desired, for increased reliability, durability and strength. In a preferred embodiment, the first and second side tabs are configured to be fixed to the second panel of the second portion, optionally wherein the first and second side tabs are fixed to an underside of the second panel of the second portion. This improves the assembly order and reduces the amount of adhesive required and production cost.

In some embodiments, the first portion and second portion each have a tapered section adjacent the fold line, wherein the first and second portion each have a reducing width relative to the remainder of the first and second portions, wherein the width is a minimum at the fold line. When the second portion is folded over the first portion, the tapered portion defines a chamfer to help guide the collar into the bag.

In some embodiments, the first panel of the first portion has a greater width than the second panel of the first portion. The difference in widths defines a shoulder between the first and second panel of the first portion that is configured to engage the top edge of the bag and locate the collar in the correct vertical location.

In some embodiments, the first and second portions each have at least one cut-out portion, optionally wherein the first panel of the first portion has a cut-out portion and the second panel of the first portion has a cut-out portion that is a mirror image of the cut-out portion of the first panel of the first portion and/or wherein the first panel of the second portion has a cut-out portion and the second panel of the second portion has a cut-out portion that is a mirror image of the cut-out portion of the first panel of the second portion. When the second panels overlie the first panels, the cut-out portions will be aligned.

In some embodiments, a fold line is defined between the first panel and the second panel of the first portion and a fold line is defined between the first panel and the second panel of the second portion, optionally wherein each fold comprises an elliptical-shaped cut-out to define a curved top surface when the first panel of the first portion overlies the second panel of the first portion and the first panel of the second portion overlies the second panel of the second portion. Advantageously, the curved surfaces can help to seat and locate an additional guiding device.

The invention also provides a method of assembling a collar adapted to support a neck portion of a bag, preferably a collection bag. The method comprising: providing a blank, the blank comprising: a first portion; a second portion configured to be folded over to overlie the first portion; a fold line located between the first and second portion, and folding the second portion to overlie the first portion.

In some embodiments, the method further comprises compressing the fold line of the blank to form an aperture between the first and second portions.

The above embodiments may be combined with any other embodiment. Embodiments that are described in combination with each other may be separated and combined with any other described embodiment.

BRIEF DESCRIPTION OF FIGURES

The invention will now be described, by way of example only, with reference to the accompanying figures, in which.

DETAILED DESCRIPTION OF FIGURES

Figure 1A:
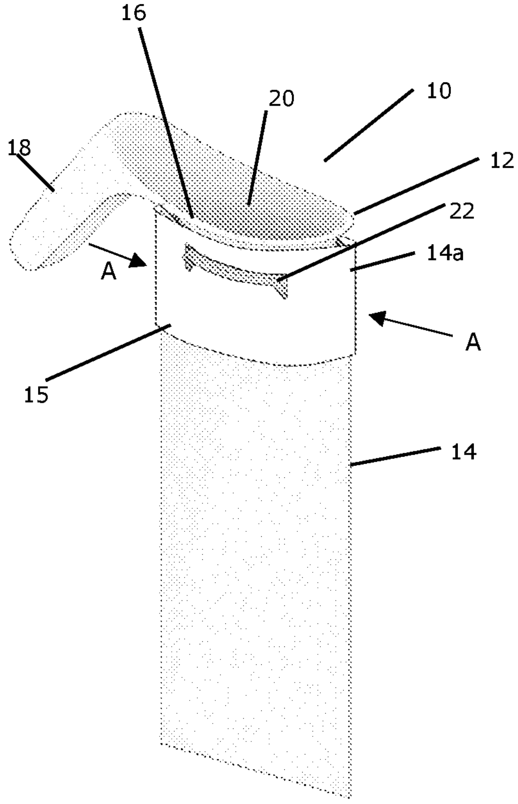
FIG. 1A shows a front view of a liquid capture device comprising a holder and a collection bag.
Figure 1B:
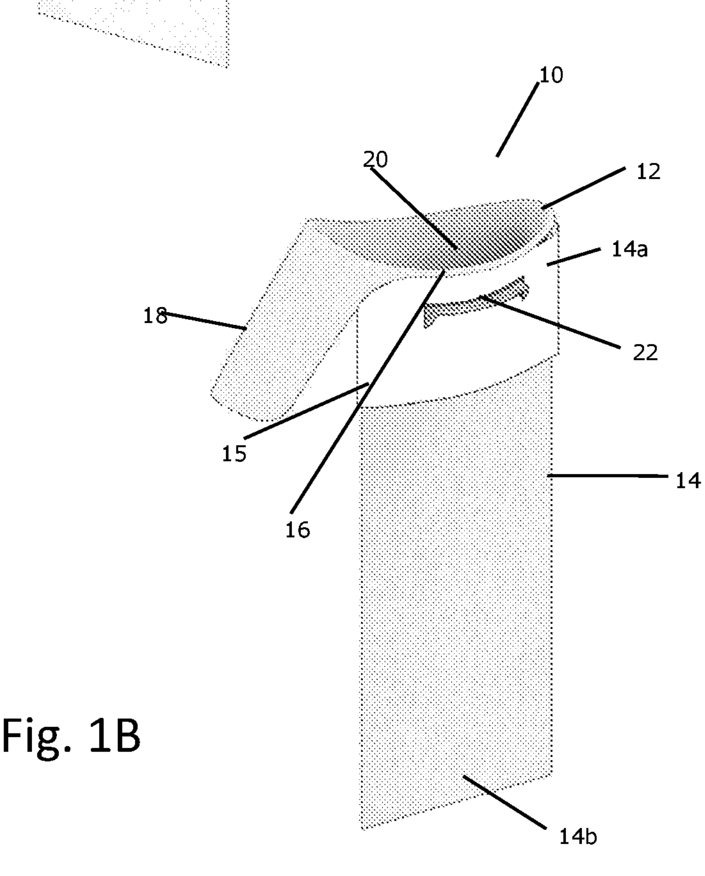
FIG. 1B shows the same device from a different angle.
Figure 2:
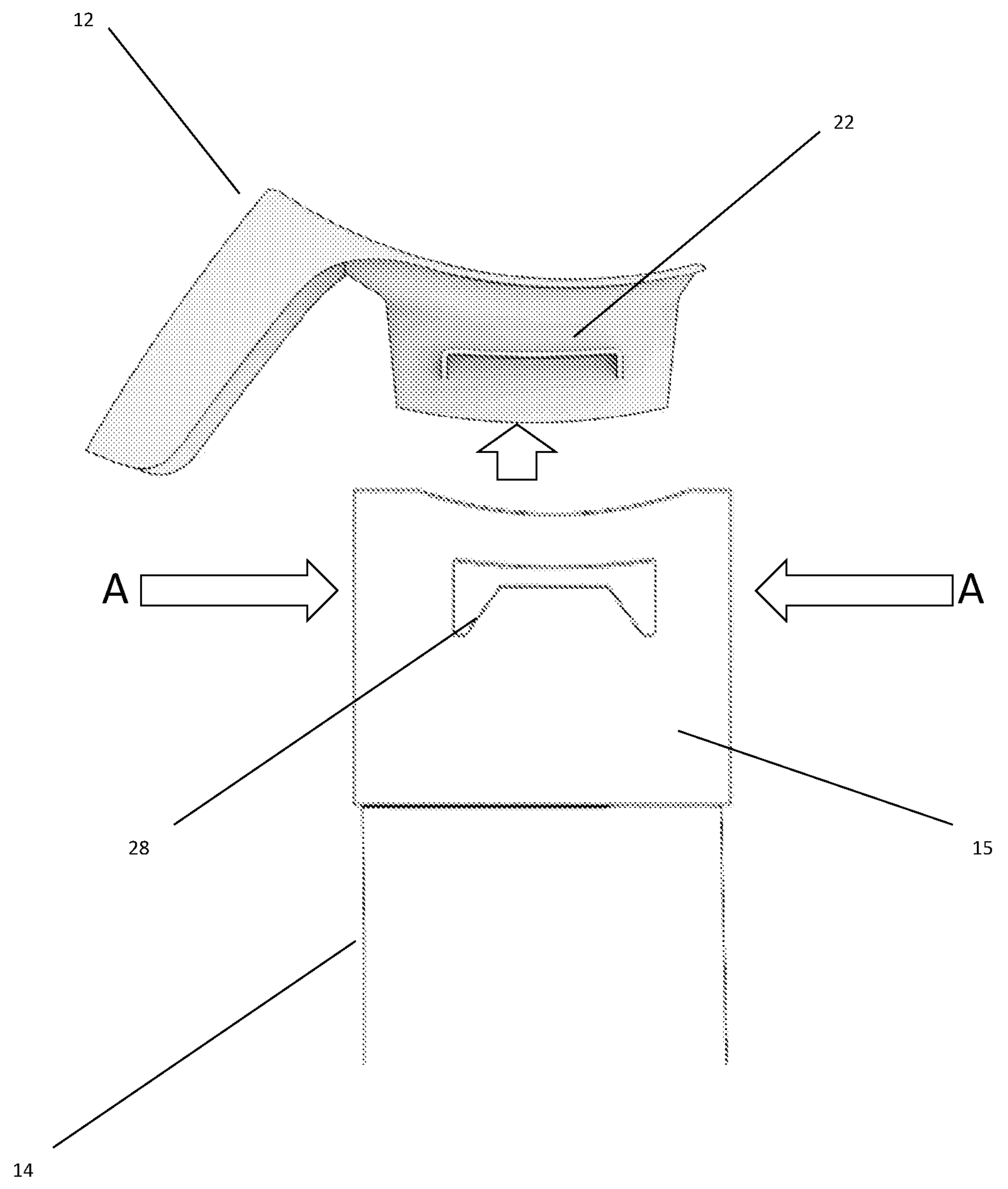
FIG. 2 shows a liquid capture device from the side. A removable attachment means is shown.

Referring to each of FIGS. 1 to 3, an embodiment of the liquid capture device of the present invention is a urine capture device 10 that comprises a holder 12, and a collection bag 14.

Figure 14:
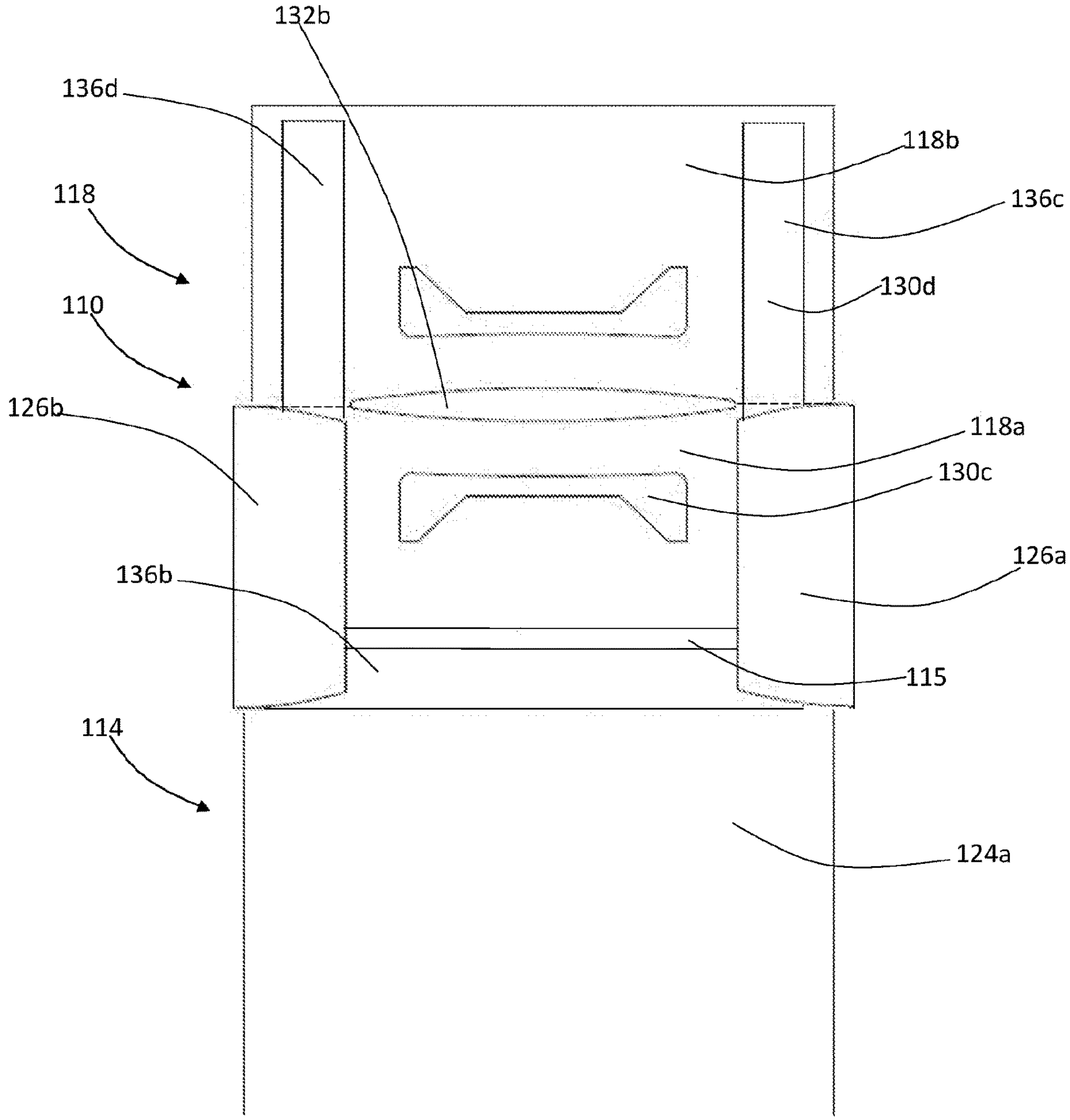

The holder 12 has a rim 16 that forms a seal with the user when in use. The holder also comprises an angled arm 18 which is conformed to provide a means for holding the device when in use. FIG. 14 *a-f* show a variety of means by which a user, depending on their level of manual dexterity and strength of grip, may hold the arm 18 in place against the pubic region when in use.

The holder 12 comprises an opening 20 to enable liquid to pass from the holder into the collection bag 14. The opening is at the bottom of a concave portion that enables the liquid to quickly drain into the collection bag.

Arrows A in FIG. 2 show how light pressure can be applied to the collar 15 to cause deformation of the collar 15. This pressure opens the collar to enable the collection bag 14 to be placed over the protrusions 22 in the holder 12. Upon releasing the pressure, the deformation in the collar 15 is reversed and the collection bag 14 is secured to the holder 12 (see FIG. 4) by way of engagement of the cut-out 28 with the protrusions 22. By re-applying very light pressure, for example by a very slight closing of only two digits, the collar 15 of the collection bag 14 deforms, causing the collar 15 to be released from the protrusions 22. This enables the user to easily attach and remove the collection bag 14 from the holder 12 without causing spillage of the liquid. Such a mechanism is easy to operate for those with reduced mobility, dexterity and/or vision, thus increasing users' independence and potentially eliminating the need for external help in managing their urinary continence.

Figure 3A:
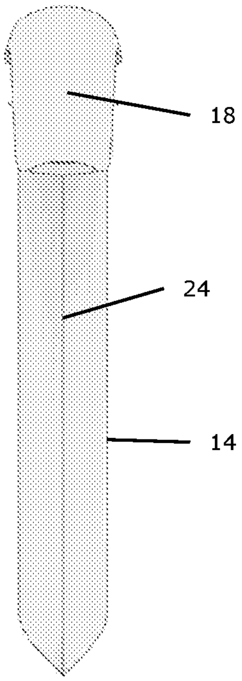
FIG. 3A shows a liquid capture device when viewed from the back showing the arm.
Figure 3B:
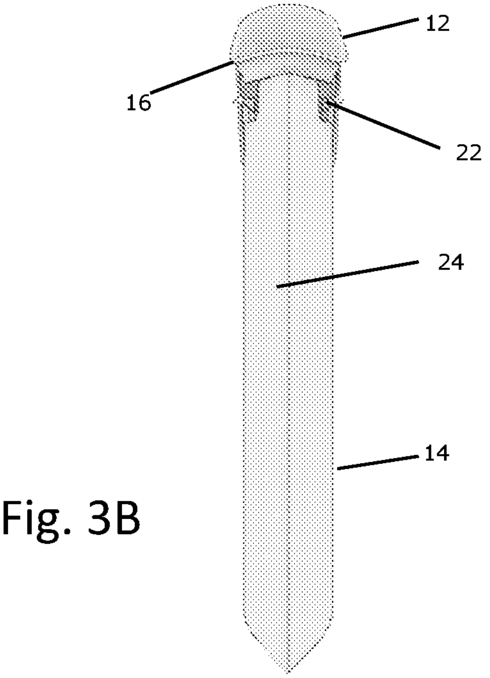
FIG. 3B shows a liquid capture device when viewed from the front.
Figure 4A:
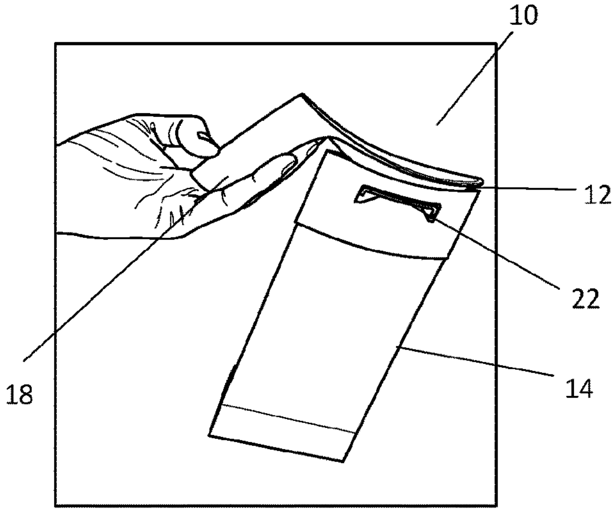
FIG. 4A-F shows different means by which a user may hold a liquid capture device in position ready for use in an orientation suited to their level of manual dexterity and strength of grip.
Figure 4B:
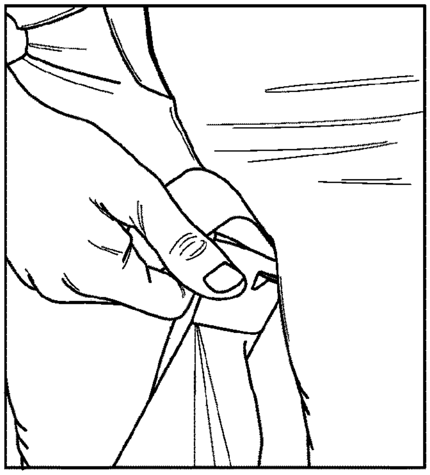
Figure 4C:
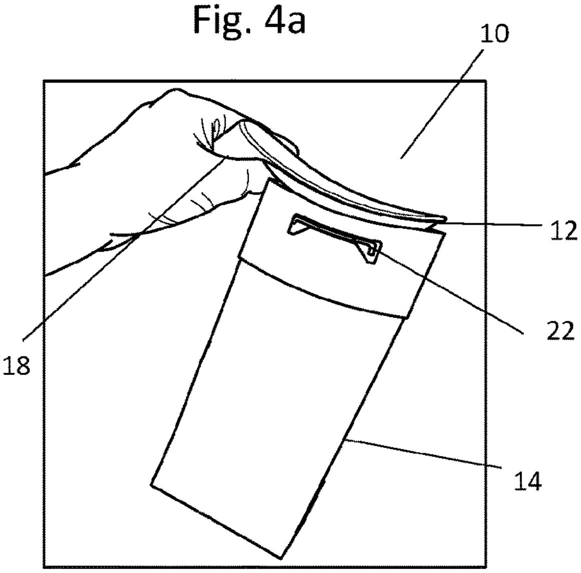
Figure 4D:
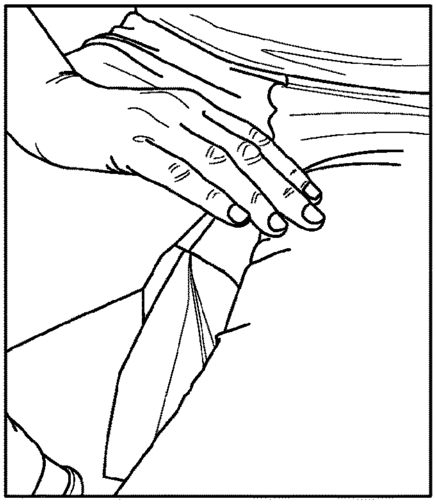
Figure 4E:
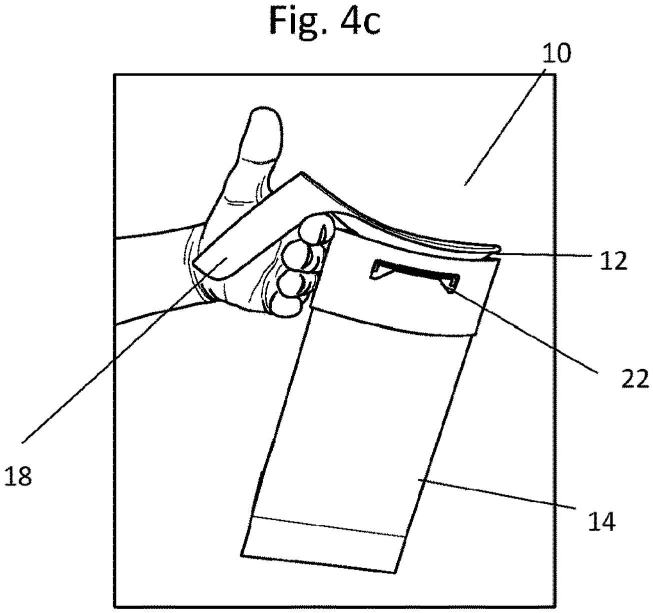
Figure 4F:
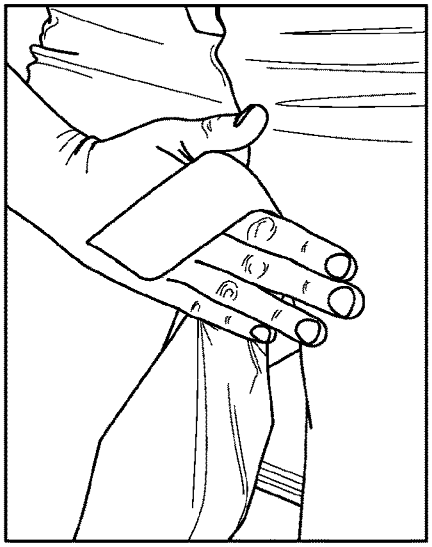

FIG. 3A shows the back of an embodiment of the collection bag 14 which does not have a gusset and FIG. 3B shows the front of the collection bag. In some embodiments, the collection bag can be made by joining together two side portions forming a seam 24 in the middle. In alternative embodiments, the collection bag may be formed as one piece.

FIGS. 4A-F shows the angled arm 18 being held by a user. The angled arm 18 improves the ability of the user to hold the device, whilst also providing guidance as to the orientation of the device when in use. The angled arm 18 provides leverage enabling those with poor musculature and/or manual dexterity to create a leakproof seal between the rim 16 of the holder 12 and the user's body when in use by applying only minimal pressure to the angled arm. As can be seen, it is possible to hold the device in a number of configurations enabling those with poor dexterity or hand strength to securely hold the device against their skin. The collection bag 14 in this embodiment has a gusset and the collar made using the blank shown in FIG. 8. However, any described embodiment of the collection bag and holder can be used.

Figure 5A:
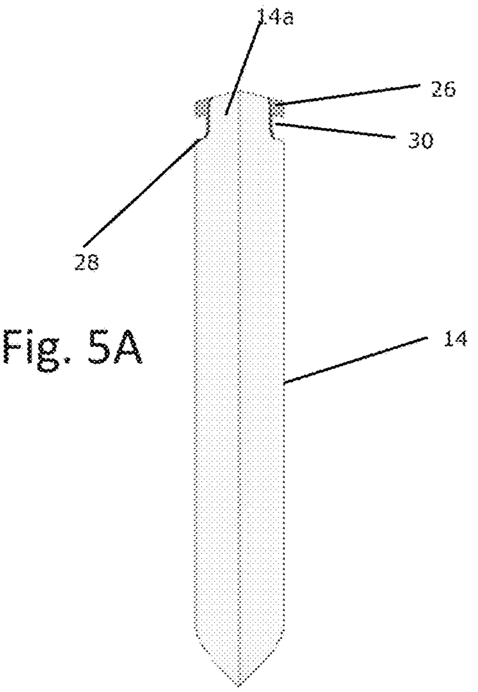
FIG. 5A shows a front or rear (end on) view of the collection bag.
Figure 5B:
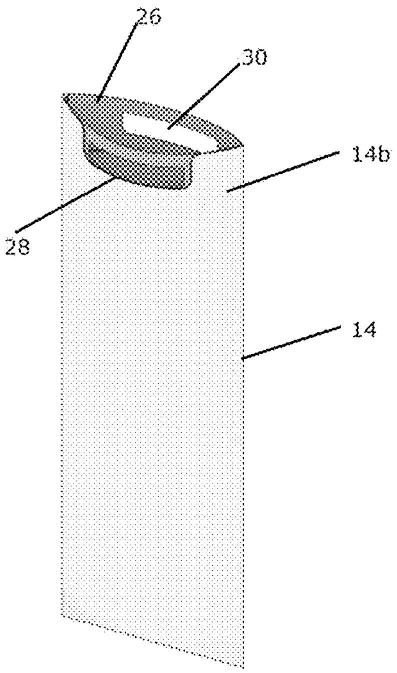
FIG. 5B shows a side view of the collection bag.
Figure 5C:
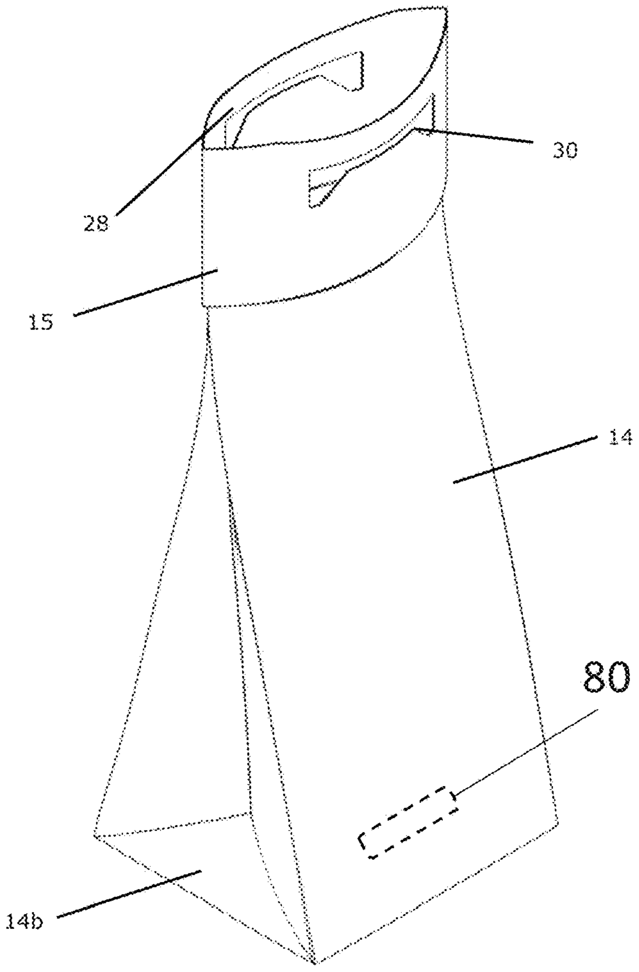
FIG. 5C shows a side view of a different embodiment of a collection bag according to the present invention.

FIGS. 5A and 5B show an example collection bag 14 of one embodiment of the present invention. The neck 14*a* of the collection bag may comprise an additional material 26 to strengthen the bag. This material may be affixed to the collection bag by any appropriate means, for example, fusing, or adhesive. The strengthening material 26 may be the same or a different material to the collection bag. Examples of the type of material are discussed above in relation to the collection bag. FIG. 5C shows an alternative embodiment wherein the collar 15 is manufactured separately to the collection bag 14 and affixed later, as described herein. The collection bag has a cut out 28 and 30 of a size conforming to protrusions 22 on the holder 12. This cut out is configured to slide over and "lock" to the complementary protrusions on the holder. This prevents the bag being able to move fore, aft, up or down relative to the holder. The strengthening material may be present in other embodiments of the device that do not use the complementary cut out and protrusion attachment means. The base 14*b* of the collection bag may be shaped to form a gusset, conformed to enable the collection bag to stand without further support. FIG. 5C also illustrates an absorbent material 80 such as described above.

Figure 6:
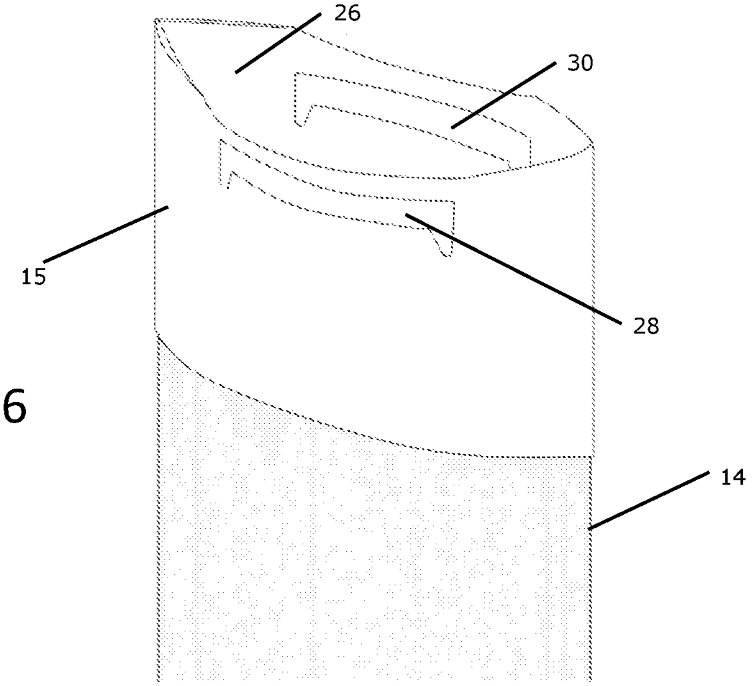
FIG. 6 shows a close up of the cut outs and neck of one embodiment of the collection bag.

FIG. 6 shows a close up of the collar 15 of the collection bag 14 shown in FIG. 5C.

Figure 7:
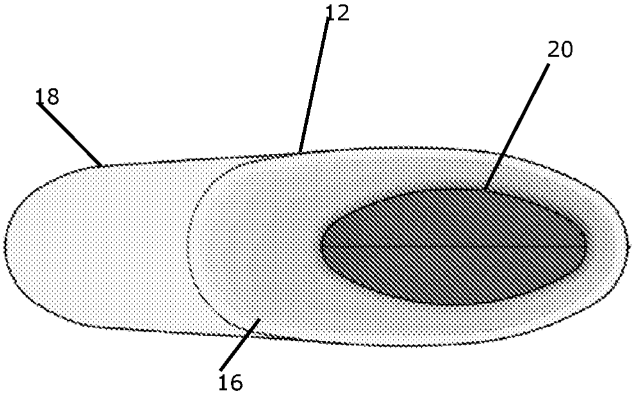
FIG. 7 shows a top view of the holder and opening therein.

FIG. 7 shows a top view of the holder 12 of an embodiment of the present invention. The holder 12, in particular the rim 16 of the holder 12, is shaped to conform to a pubic region of a user. The holder 12 comprises a concave portion which forms a cavity into which the liquid is initially received during use and directed towards the opening 20.

Figure 8:
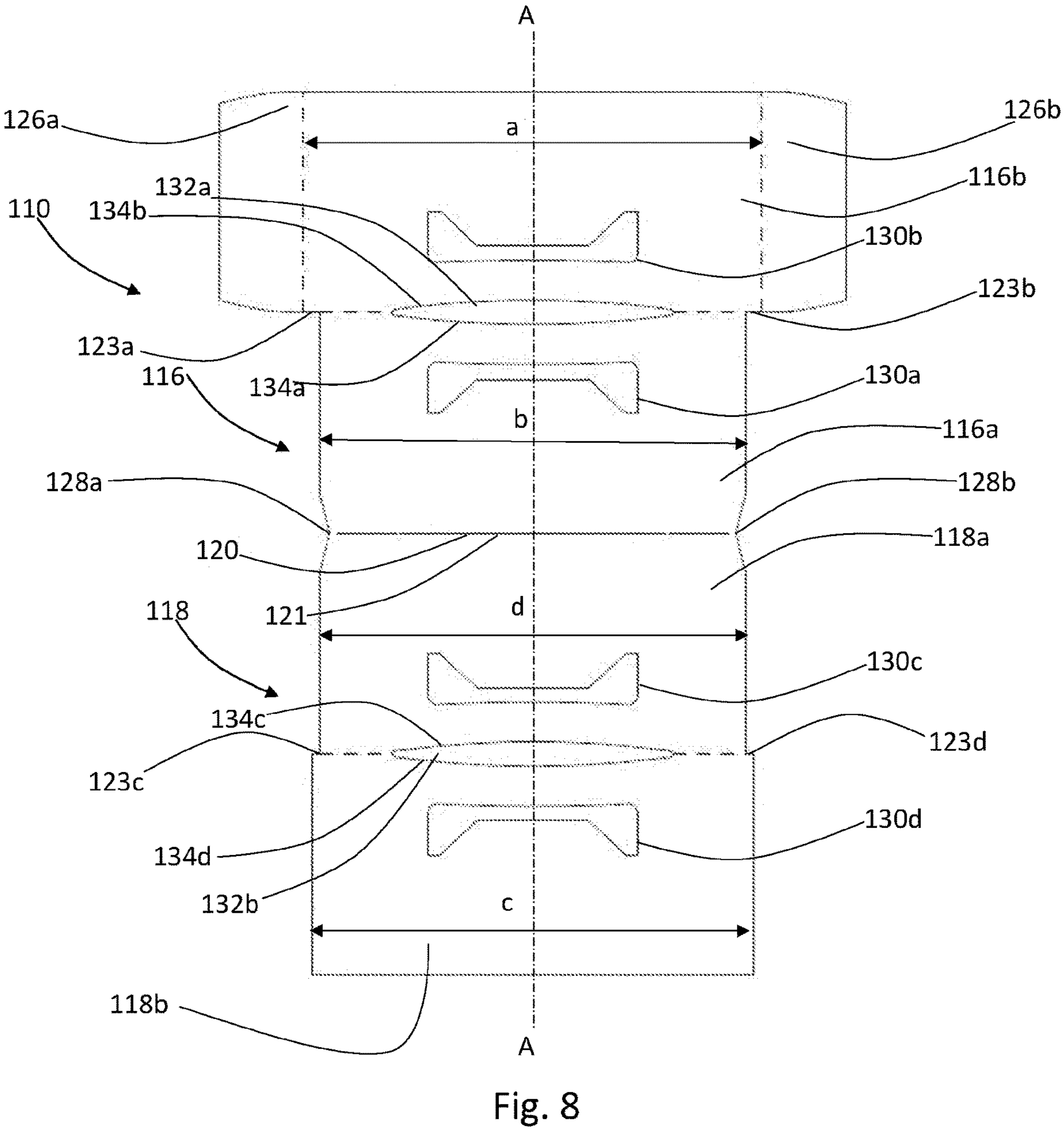
FIG. 8 is a front view of a blank for forming a collar adapted to support a neck portion of a collection bag according to an embodiment of the present teachings.
Figure 9A:
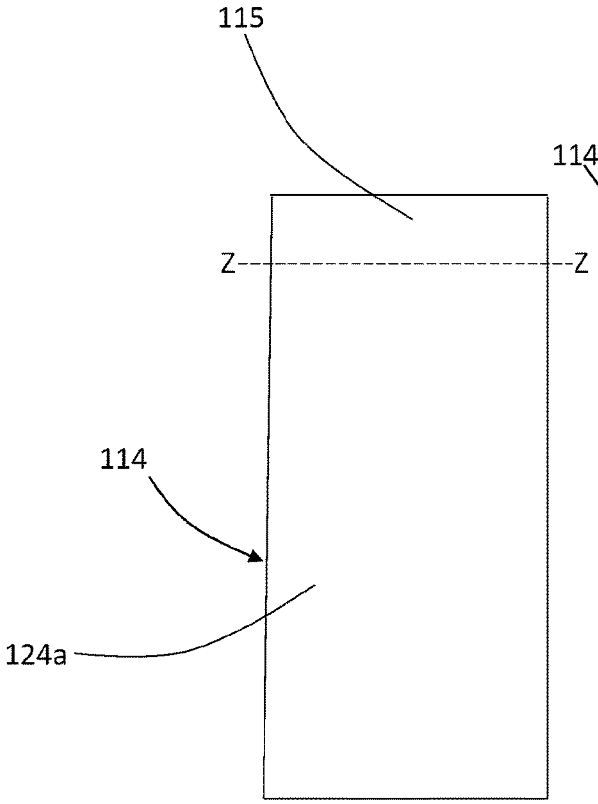
FIG. 9*a* shows a front view of a collection bag according to an embodiment of the present teachings.
Figure 9B:
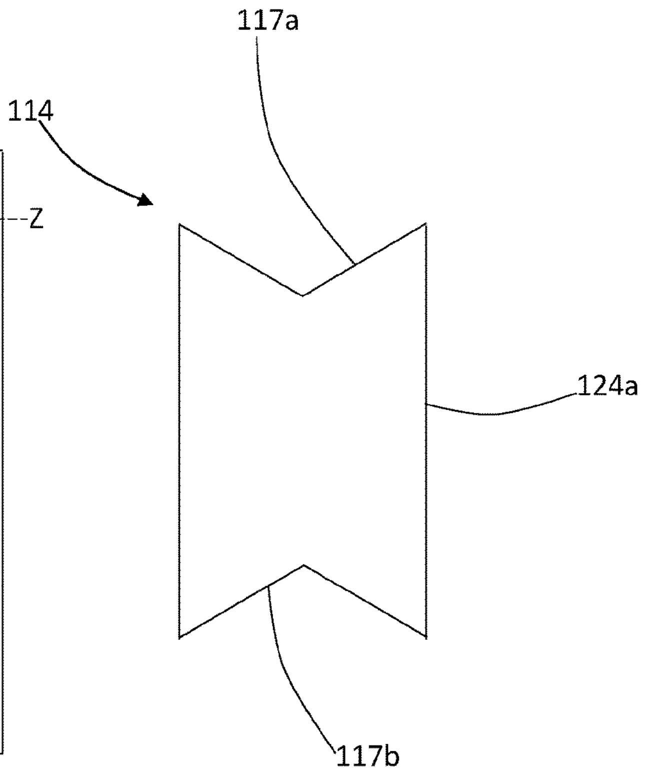
FIG. 9*b* shows a top view of a collection bag according to an embodiment of the present invention.

FIG. 8 shows a blank generally indicated at 110. Shown most clearly in FIG. 17, the blank 110 is for forming a collar 112 adapted to support a neck portion 115 of a collection bag 114. The collection bag 114 of this embodiment is suitable for collecting urine. In other embodiments, however, the collection bag 114 may be suitable for collecting other material, as desired.

The blank 110 is cut from a sheet material, for example, but not limited to, a polymer, card or paper. The blank 110 includes a first portion 116, a second portion 118 and a fold line 120. The fold line 120 is located between the first and second portions 116, 118. The second portion 118 is configured to fold over and overlie the first portion 116. When the fold line 120 is compressed, an aperture 124 (see FIG. 16) is defined between the first and second portion 116, 118.

Figure 16:
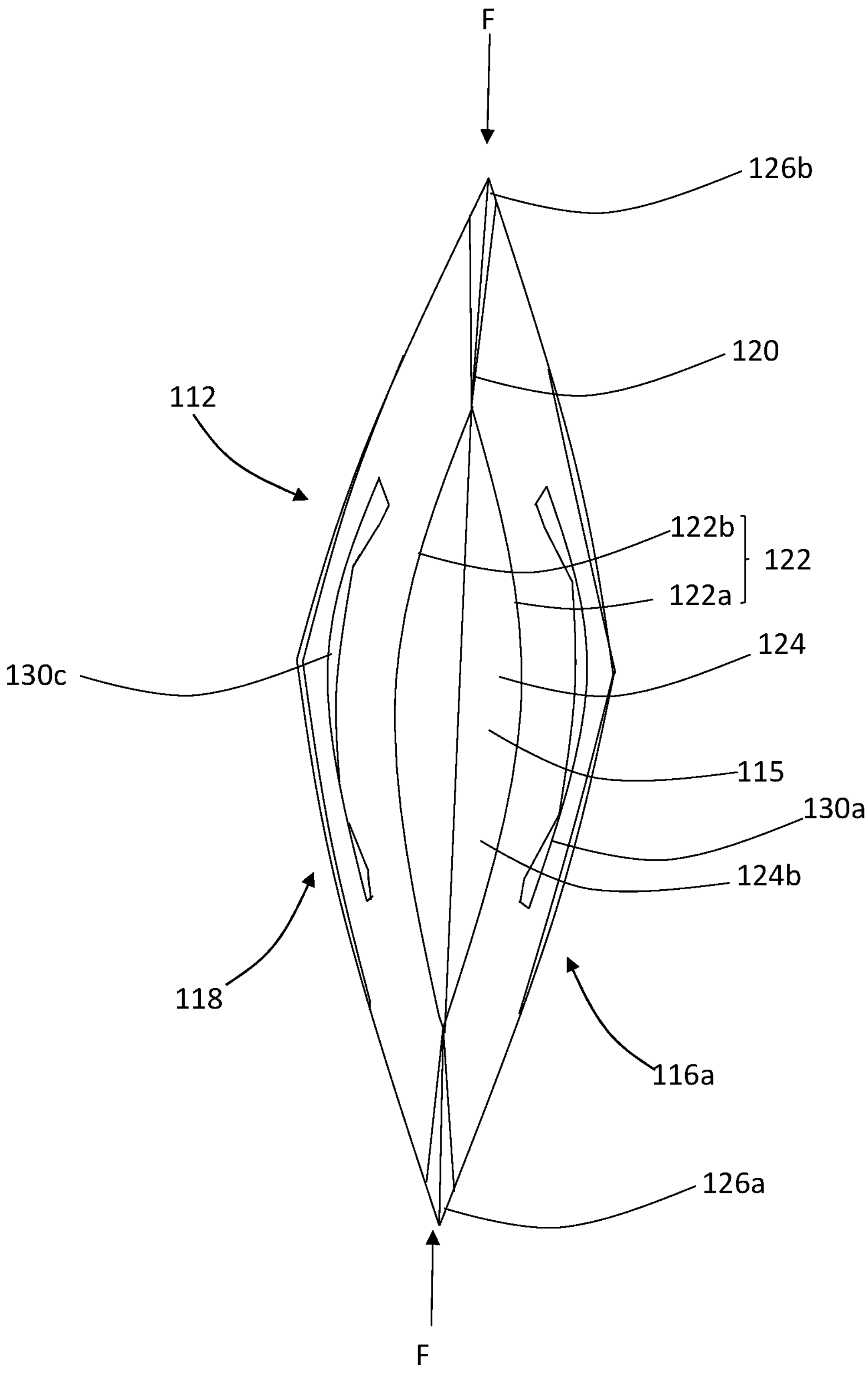
FIG. 16 shows a top view of the collar of FIG. 8.

In this embodiment, a through cut 121, 132*a* (FIG. 11) is defined on the fold line 120. The through cut 132*a* passes through the depth of the blank 110. The through cut is configured to expand in a direction perpendicular to the fold line 120 as the fold line 120 is compressed, to define the aperture 124 (FIG. 16). The aperture 124 creates a path through the collar 112 such that material, such as urine, can pass through the neck portion 115 and into the collection bag 114.

The fold line 120 extends in a direction perpendicular to the longitudinal axis A-A. The through cut is located centrally with respect to the fold line 120 and extends along the majority of the fold line 120. In this embodiment, the fold line 120 includes a frangible portion 121, the frangible portion 121 forming the through cut 122 (FIG. 16) as the fold line is compressed. In this embodiment, the frangible portion 121 is a perforated line. However, in alternative embodiments any suitable frangible portion may be used, for example a score line. In alternative embodiments the through cut 132*a* may be pre-formed in the fold line 120.

In some embodiments, the frangible portion 121 provides a means of retaining solid or semi-solid materials inside the collection bag until the frangible closure is broken by compression.

In this embodiment, the first portion 116 and the second portion 118 are substantially T-shaped (FIG. 8). Put another way, a width a of the first portion 116 at a first end is greater than a width b of the first portion 116 at a second end, and a width c of the second portion 118 at a first end is greater than a width d of the second portion 118 at a second end.

In this embodiment, the first portion 116 includes a first panel 116*a* and a second panel 116*b*. The second portion 118 includes a first panel 118*a* and a second panel 118*b*. The first and second panels 116*a*, 116*b*, 118*a*, 118*b* are substantially rectangular. The second panels 116*b*, 118*b* are configured to be folded to overlie the respective first panels 116*a*, 118*a*. This provides extra rigidity to the collar 112 and the neck portion 115 of the collection bag 114. The first panels 116*a*, 118*a* are connected by the fold line 120 such that the fold line 120 extends along a first side of the first panel 116*a* of the first portion 116 and a first side of the first panel 118*a* of the second portion 118. The second panels 116*b*, 118*b* are connected to a second side of the first panels 116*a*, 118*a* opposing the first side. In this embodiment, the first and second panels 116*a*, 118*a*, 116*b*, 118*b* share a common central longitudinal axis, the axis A-A.

In order for the first and second portions 116, 118 to have the substantially T-shaped configuration, the second panels 116*b*, 118*b* have a greater width than the first panels 116*a*, 116*b*. For example, the first panels 116*a*, 118*a* may have a width in the range 50 mm to 170 mm, e.g., in the range 100 mm to 120 mm. The second panels 116*b*, 118*b* may have a width in the range 50 mm to 170 mm, e.g., in the range 100 mm to 120 mm. It shall be appreciated that any suitable width of first and second panels 116*a*, 118*a*, 116*b*, 118*b* may be used. In this embodiment, the width of the second panel 116*b* of the first portion 116 is greater than the width of the second panel 118*b* of the second portion 118. This helps to connect the first and second portions 116, 118 when the collar 112 is assembled.

The difference in the widths of the panels 116*a*, 116*b*, 118*a*, 118*b* defines a plurality of shoulders 123*a-d* located at opposing sides of both the first and second portions 116, 118. The shoulders 123*a-d* are intended to locate on a top edge of the neck portion 115 when the collar 112 is assembled. This helps to ensure that the collar 112 is inserted a predetermined distance into the collection bag 114.

Figure 13:
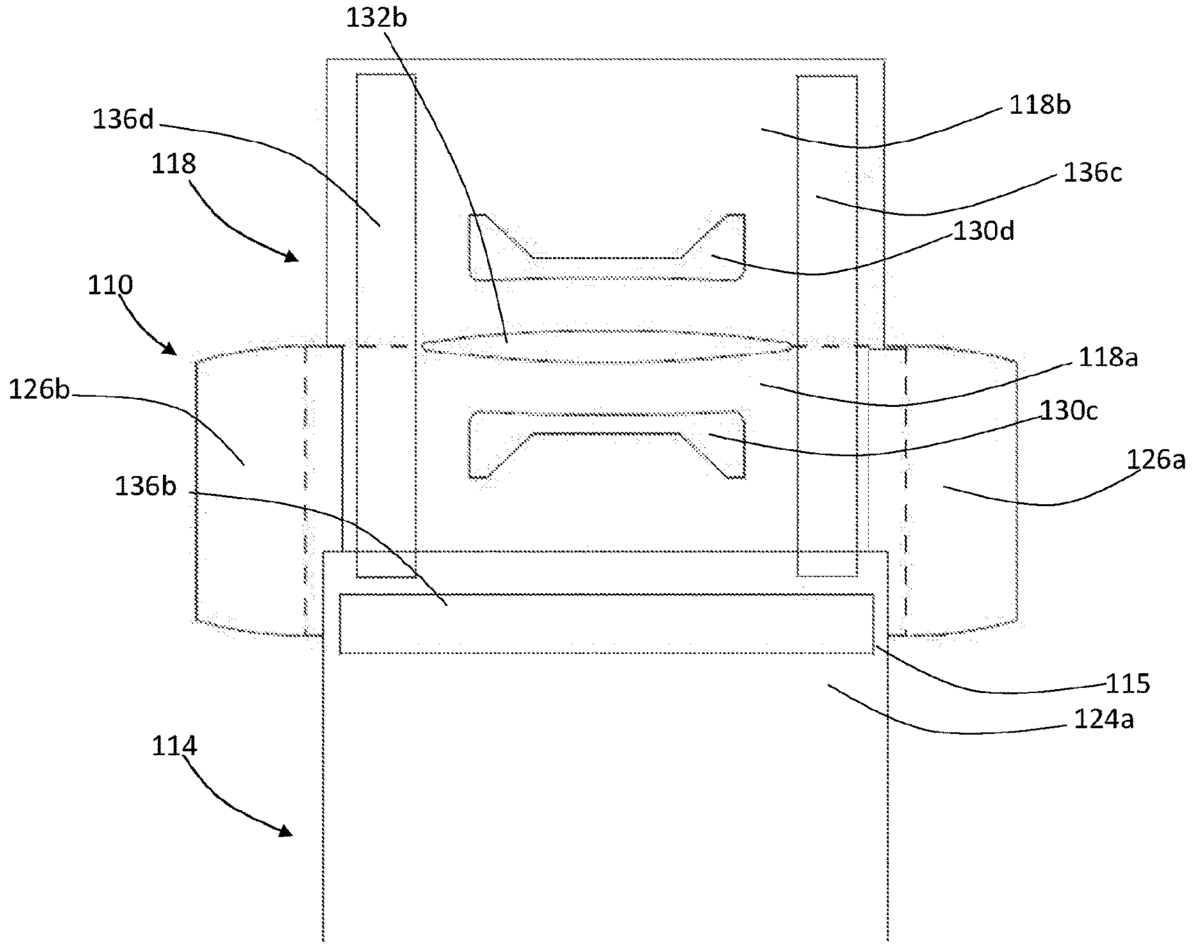

When the collar is assembled and located on the neck portion 115 of the collection bag 114 (FIG. 15), an underside of the first panel 116*a* of the first portion 116 and an underside of the first panel 118*a* of the second portion 118 are configured to engage an internal surface 124*b* of the neck portion 115. An underside of the second panel 116*b* of the first portion 116 and an underside of the second panel 118*b* of the second portion 118 is configured to engage an external surface 124*a* of the neck portion 115. Put another way, the neck portion 115 is located in between the first panels 116*a*, 118*a* and the second panels 116*b*, 118*b* (FIG. 13).

Figure 15:
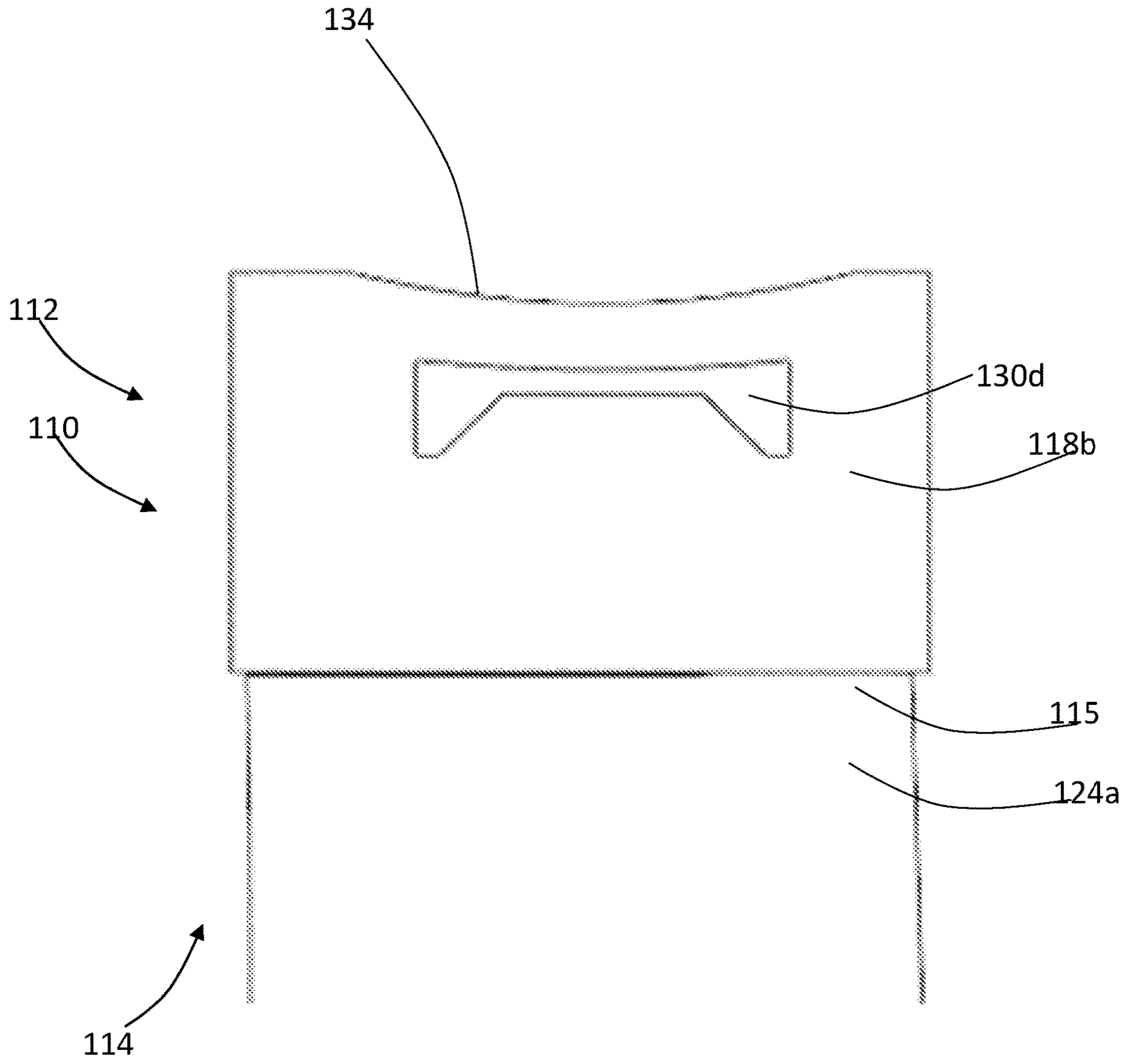
FIG. 15 shows a front view of a collar assembled from the blank of FIG. 8.

The blank 110 further includes side tabs 126*a*, 126*b* and a tapered portion 128*a*, 128*b* (FIG. 8). When the collar 112 is assembled, the side tabs 126*a*, 126*b* extend between the first portion 116 and the second portion 118 so as to form a continuous collar 112 (FIG. 15). In this embodiment, the side tabs 126*a*, 126*b* project from the second panel 116*b* of the first portion 116 and are fixed to the second portion 118 by an adhesive. The side tabs 126*a*, 126*b* are located in-between the first panel 118*a* and the second panel 118*b* of the second portion 118. The side tabs 126*a*, 126*b* are also located between the external surface 124 of the neck portion 115 and the second portion 118*b*. When the collar 112 is assembled, the first and second side tabs 126*a*, 126*b* are fixed to the underside of the second panel 118*b* of the second portion 118. In other embodiments, however, the first and second side tabs 126*a*, 126*b* may be fixed to a top surface of the second panel 118*b* of the second portion 118, or alternatively only to the neck portion 115 of the collection bag 114.

The tapered portions 128*a*, 128*b* are located adjacent the fold line 120 (FIG. 8). At the tapered portions 128*a*, 128*b*, the width of the blank 110 tapers to a minimum width at the fold line. The first and second portions 116, 118 each have a reducing width relative to a remainder of the first and second portion 116, 118. The width is a minimum at the fold line 120. The tapered portion 128*a*, 128*b* is symmetrical about the fold line 120, and about the central longitudinal axis A-A of the blank 110. When the second portion 118 is folded over the first portion 116, the tapered portion defines a chamfer to help guide the collar into the bag. The tapered portion 128*a*, 128*b* is substantially linear, however in alternative embodiments the tapered portion 128*a*, 128*b* may be any suitable shape; for example, curved.

Figure 17:
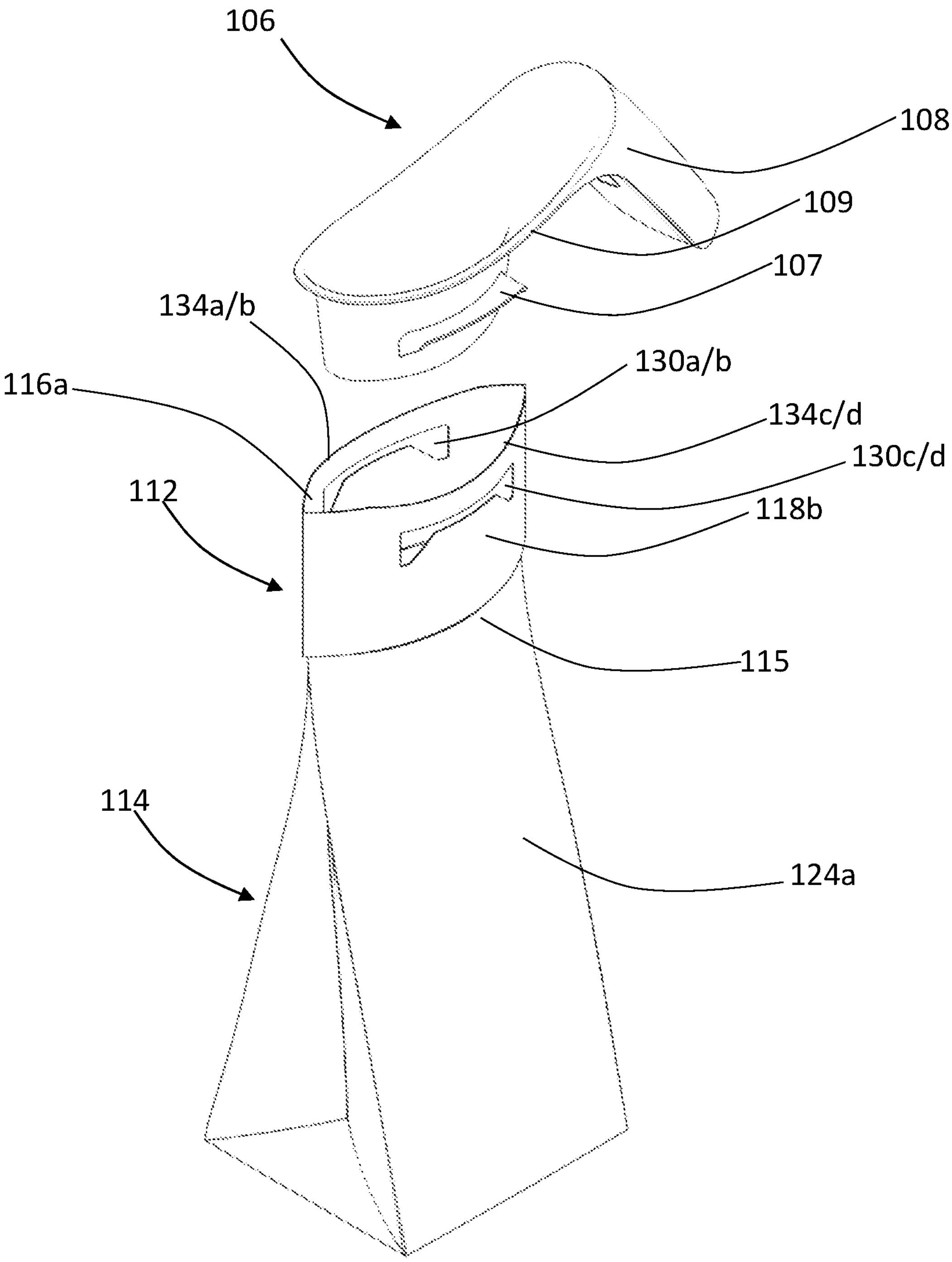
FIG. 17 shows an isometric view of the collar of FIG. 8, the collection bag of FIG. 9 and the handle.

The blank 110 further includes at least one cut-out 130*a-d* (FIG. 8) for receiving a holder 106 (FIG. 17), and an aperture 132. The arm 108 of the holder 106 provides a means for holding the device when in use. Liquid passes through the holder 106 and into the collection bag 114 (FIG. 17).

In this embodiment, the blank 110 includes four cut-outs 130*a-d*. Two of the cut-outs 130*a*, 130*b* are located on the first portion 116, and two of the cut-outs 130*c*, 130*d* are located on the second portion 118.

Specifically, the first cut-out 130*a* is located on the first panel 116*a* of the first portion 116, and second cut-out 130*b* is located on the second panel 116*b* of the first portion 116, the third cut-out 130*c* is located on the first panel 118*a* of the second portion 118, and/or the fourth cut-out 130*d* is located on the second panel 118*b* of the second portion 118. The first and second cut-outs 130*a*, 130*b* are located symmetrically about the fold line 120 between the first and second panels 116*a*, 116*b* of the first portion 116. The third and fourth cut-outs 116*c*, 116*d* are located symmetrically about a fold line between the first and second panels 118*a*, 118*b* of the second portion 118. The cut-outs 130*a-d* being located symmetrically means that when the respective second portions 116*b*, 118*b* are folded over the respective first portions 116*a*, 116*b*, the first and second cut-outs 130*a*, 130*b*, and the third and fourth cut-outs 130*c*, 130*d* are aligned to receive the handle 108 of the device 106 (FIG. 17).

Figure 10:
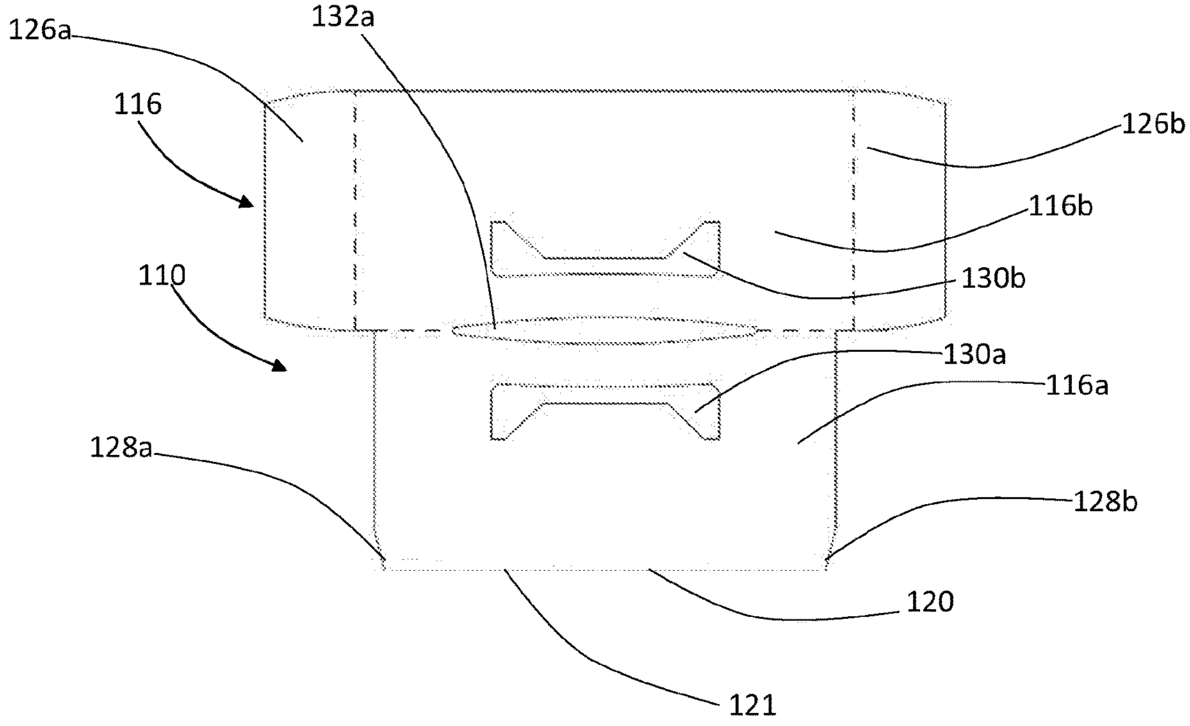
FIGS. 10 to 14 show a front view of the blank of FIG. 8 in partially assembled states.

The cut-outs 130*a-d* are located centrally, although this is not essential and are aligned along the longitudinal axis of the blank 110. Each cut-out 130*a-d* includes an elongate slot, and an aperture located at each end of the elongate slot. As illustrated in FIG. 10, the shape of cut-outs 130*a-d* corresponds to the shape of a protrusion 107 located on the holder 106 (FIG. 17).

In this embodiment, the blank 110 includes two apertures 132*a*, 132*b* for locating the device 106. The first aperture 132*a* is located on the first portion 116, and the second aperture 132*b* is located on the second portion 118. The first aperture 132*a* is located on the fold line between the first and second panels 116*a*, 116*b* of the first portion 116, and the second aperture 132*b* is located on the fold line between the first and second panels 118*a*, 118*b* of the second portion 118. The first and second apertures 132*a*, 132*b* are symmetrical about the fold lines of the first portion 116 and the second portion 118.

The first and second apertures 132*a*, 132*b* define a curved top surface when the first and second panels 116*a*, 118*a*, 116*b*, 118*b* are folded over, the curved top surface helping to seat the collection bag 114 on the holder 106 (FIG. 17) and avoiding interference that might otherwise impair the performance of the device. The first and second apertures 132*a*, 132*b* each include a first curved boundary 134*a*, 134*b*, wherein the curve extends towards the first portion 116*a*, 118*a* and a second curved boundary 134*c*, 134*d*, wherein the curve extends towards the second portion 116*b*, 118*b*. The first and second curved boundaries 134*a-d* define the curved top surface. As illustrated in FIG. 17, the holder 106 includes a curved shoulder 109, which corresponds to the curve of the top surface of the collection bag 114.

In an alternative embodiment, the second panels 116*b*, 118*b* may be omitted. In the embodiment omitting the second panels 116*b*, 118*b*, the first and second portions 116, 118 may be fastened to the internal or external surface 124*b*, 124*a* of the neck portion 115 of the collection bag 114.

In a further alternative embodiment, the second panels 116*b*, 118*b* may be in the form of tabs extending from a top edge of the first panel 116*a* and a bottom edge of the first panel 118*a*. In this embodiment, the second panels may be folded over and secured to the neck portion 115 of the collection bag 114.

Alternatively, the second panels 116*b*, 118*b*, may extend from a side edge of the first panels 116*a*, 118*a*. In this embodiment, the fold lines between the first and second panels 116*a*, 118*a*, 116*b*, 118*b* extend in a direction generally parallel to a longitudinal axis of the bag. The second panels 116*b*, 118*b* may extend from either side of the first panels 116*a*, 118*a*. For example, the second panels 116*b*, 118*b*, may both extend from the same side of the first panels 116*a*, 118*a*, or alternatively the second panels 116*b*, 118*b* may extend from opposing sides of the first panels 116*a*, 118*a*. In this embodiment, the blank may include a side tab for extending between the first and second portions, and two top tabs for extending between the first and second panels of the first portion and the second portion.

In a further alternative embodiment, the side tabs 126*a*, 126*b* may be positioned at any suitable location on the blank 110. For example, the side tabs 126*a*, 126*b* may be positioned on the second portion 118. Alternatively, one of the side tabs 126*a* may extend from a first side of either of the first panels 116*a*, 118*a*, and one of the side tabs 126*b* may extend from an opposing second side of either of the second panels 116*a*, 118*a*. Any suitable number of side tabs may be used, for example two side tabs on each side of the blank 110.

In a further alternative embodiment, the side tabs 126*a*, 126*b* may be omitted altogether and any suitable mechanism for connecting the first and second portions 116, 118 may be used, for example an adhesive connection. Alternatively, the side tabs 126*a*, 126*b* may be provided separately and secured to the first and/or second portion 116, 118 using an adhesive when the collar 112 is formed from the blank 110.

It shall be appreciated that in alternative embodiments, the tapered portion 128*a*, 128*b*, and/or at least one cut-out 130*a-d* and/or the aperture 132*a*, 132*b* may be omitted. Alternatively, any number of cut-outs and/or apertures of any suitable shape may be used depending on the shape of the device.

Figure 11:
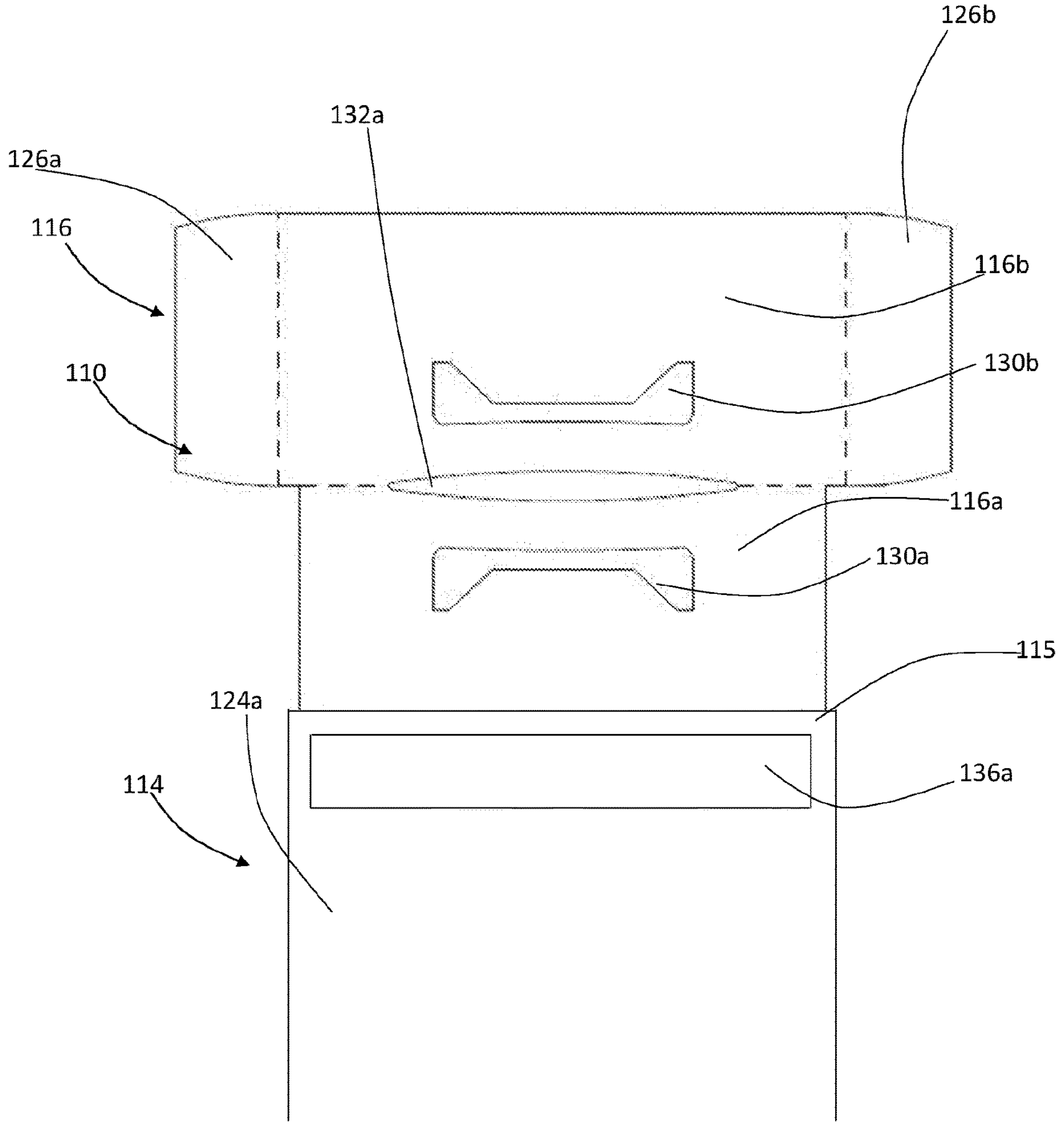

With reference to FIGS. 10 to 14, a method of assembling the collar 112 from the blank 110 is described hereafter. The method will be described in relation to the embodiment of FIG. 8; however it shall be appreciated that the alternative embodiments described above may use substantially the same, or a similar method. As illustrated in FIG. 11, the blank 110 is folded about the fold line 120 such that the second portion 118 overlies the first portion 116. The folded blank 110 is then located within the neck portion 115 of the collection bag 114 such that the first panels 116*a*, 118*a* are located within the neck portion 115. The underside of the first panels 116*a*, 118*a* is secured to the internal surface 124*b* of the neck portion 115 using an adhesive (not shown).

Figure 12:
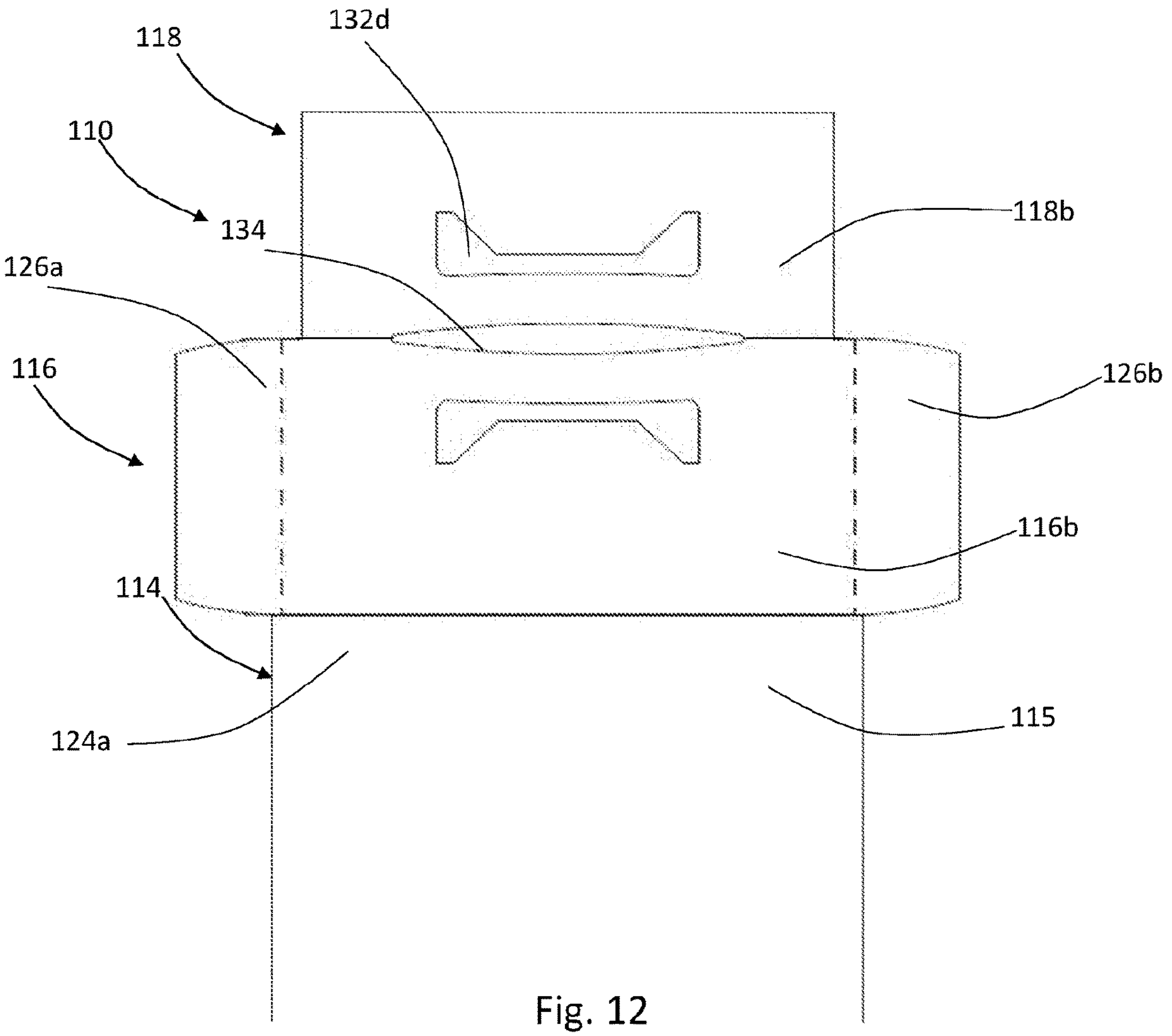

As illustrated in FIG. 11, an adhesive 136*a* is applied to the external surface 124*a* of the neck portion 115 on the first side of the neck portion 115. In this embodiment, a first adhesive strip 136*a* is secured towards a top edge of the neck portion 115. The blank 110 is lowered into the neck portion 115 such that the shoulders 123*a-d* sit above the top edge of the neck portion 115 so as to enable enough material to fold around the collection bag 114, whilst leaving the apertures unobscured. The underside of the second panel 116*b* is folded over the first panel 116*a* and secured to the external surface 124*a* of the neck portion 115 by the first adhesive strip 136*a*, as illustrated in FIG. 12.

As illustrated in FIG. 13, a second adhesive strip 136*b* is applied to a second side of the neck portion 115 in a substantially equivalent location to the first adhesive strip 136*a*. Third and fourth adhesive strips 136*c*, 136*d* are applied to the underside of the second portion 118 towards each of the opposing side edges. Put another way, the third and fourth adhesive strips 136*c*, 136*d* are located adjacent the first and second tabs 126*a*, 126*b* when the blank 110 is in the partially assembled state of FIG. 13. The third and fourth adhesive strips 136*c*, 136*d* extend along a majority of the side edges of the second portion 118, and onto the external surface 124*a* of the neck portion 115.

FIG. 14 shows the side tabs 126*a*, 126*b* being folded over the second side of the neck portion 115 and fixed to the underside of the second portion 118 by the second, third and fourth adhesive strips 136*b-d*. The second panel 118*b* is folded over the first panel 118*a*. As the third and fourth adhesive strips 136*c*, 136*d* extend over the externally facing surface of the second panel 118, the adhesive strips 136*c*, 136*d* are used to fix the side tabs 126*a*, 126*b* to the first panel 118*a*, as well as to fix the second panel 118*b* to the side tabs 126*a*, 126*b*.

The arrangement of the first and second portions 116, 118, as well as the side tabs 126*a*, 126*b* and the adhesive 136*a-d* minimises the required amount of adhesive and simplifies the assembly process. Locating the adhesives as described prevents the adhesive from obstructing the cut-outs 130*a-d* whilst helping to ensure the perimeter of the blank 110 is secured to the collection bag 114.

A force is applied in a direction substantially parallel to the fold line 120. For example, the force F may be applied by the user squeezing the ends of the collar 112 towards each other, as illustrated in FIG. 16. As the fold line is provided with the frangible portion 121 (i.e. a region of reduced strength) (see FIG. 8), the force breaks the frangible points 121, thus creating the aperture 124 (FIG. 16) through which material can pass into the neck portion 115. The strength of the frangible portion may be varied, for example, by including fewer perforations, or reinforcing the area with additional material.

In an alternative method of assembly, the side tabs 126*a*, 126*b* may be fixed to the externally facing surface of the second panel 118*b*.

It shall be appreciated that in alternative embodiments, for example the alternatives outlined above, the method of assembling the collar 112 may be modified to accommodate the alternative features.

For example, in the embodiment where the second panels 116*b*, 118*b* extend from the sides of the first panels 116*a*, 118*a*, the order of folding the panels 116*a*, 116*b*, 118*a*, 118*b* would differ. However, the method would still result in a collar adapted to support the neck portion 115 of the collection bag 114.

Figure 18A:
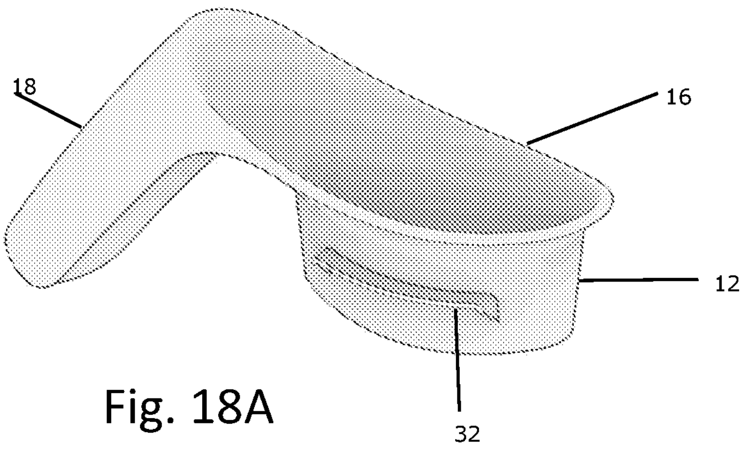
FIGS. 18A-C show various views of an embodiment of the handle of the present invention.
Figure 18B:
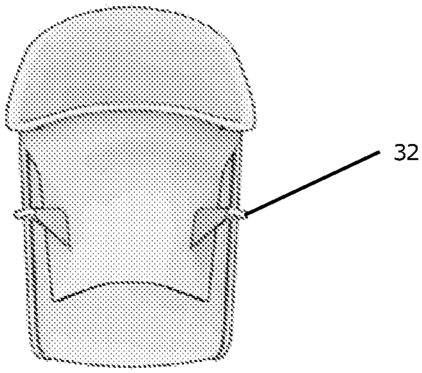
Figure 18C:
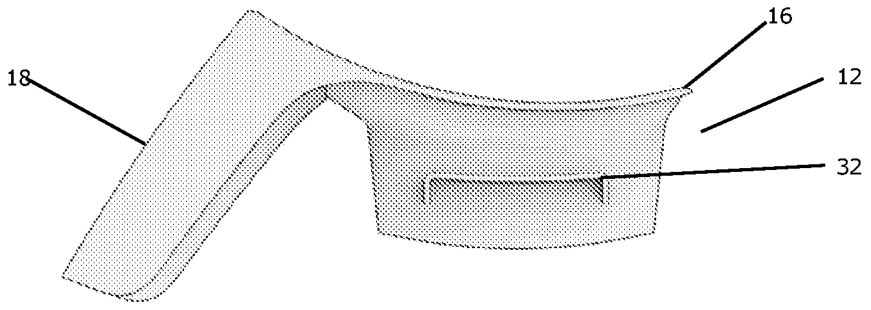
Figure 19:
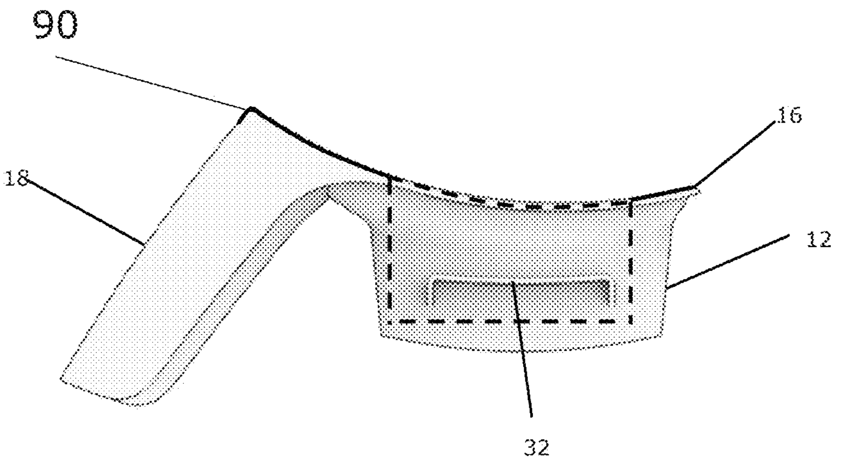
FIG. 19 is the view of the handle of FIG. 18C with an insert shown schematically attached to the handle.
Figure 20:
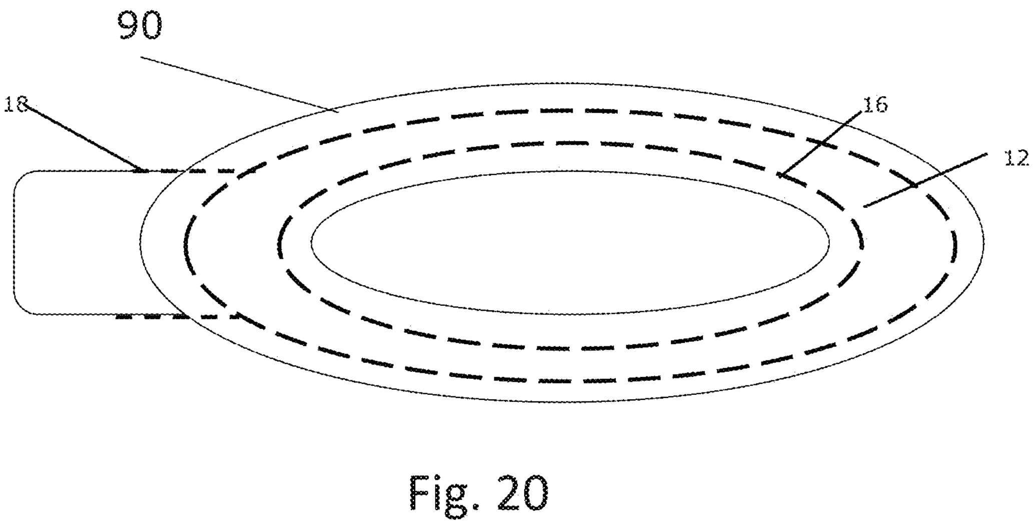
FIG. 20 is a top plan view of the handle with the insert.
Figure 21:
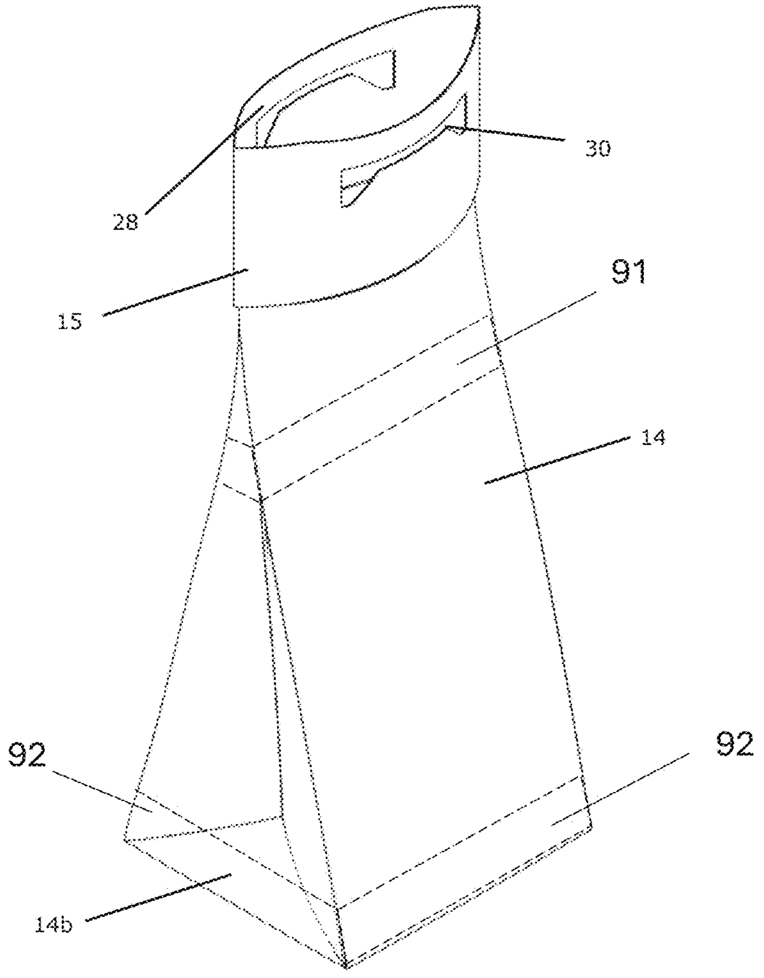
FIG. 21 is a side view of the collection bag in accordance with an embodiment of the present teachings.
Figure 22:
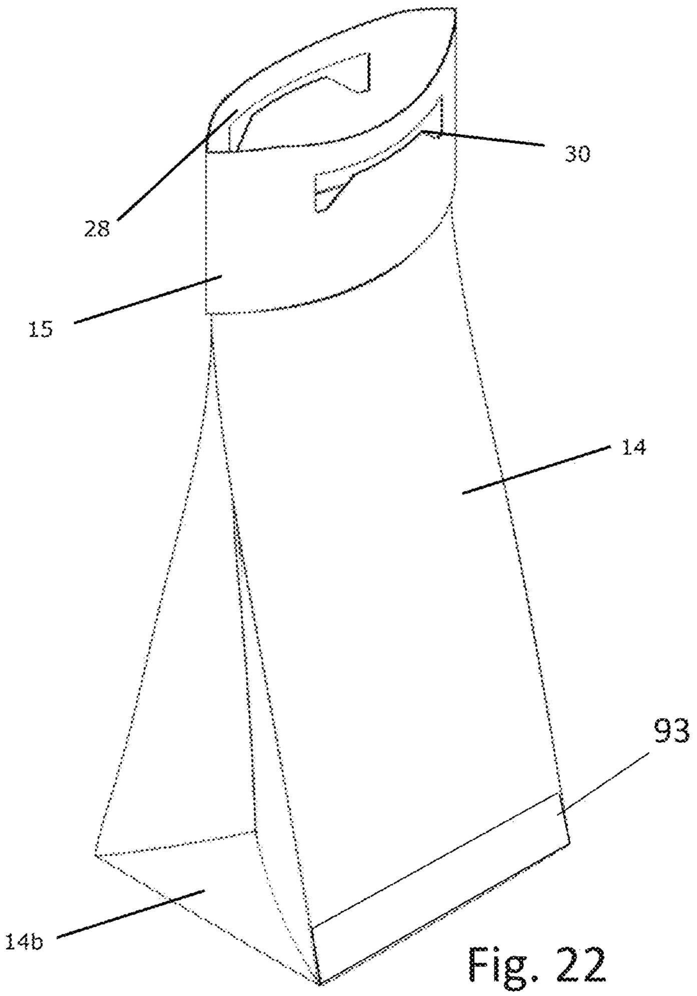
FIG. 22 is a side view of the collection bag in accordance with an embodiment of the present teachings.

FIGS. 18A and 18B show the complementary protrusions 32 on the holder 12 of the device. These protrude from the holder 12 to provide a "ledge" or "platform" for the complementary cut outs 28, 30 in the collection bag 14 to sit on (see FIG. 5). In some embodiments, the protrusions 32 are at an acute angle to the sides of the holder 12 to provide a recessed "seat" for the cut outs to sit in. In some embodiments, there is also sufficient friction between the external surface of the holder and the internal surface of the collection bag 14 to secure the collection bag to the holder 12. FIG. 19 illustrates an insert 90 adapted to fix to the holder 12. FIG. 20 is a top-down view of the insert 90 and the holder 12. FIG. 21 illustrates the collection bag 14 with a first super absorbent polymer 91 attached to an upper region of the collection bag 14 and a second super absorbent polymer 92 attached to a bottom part of the collection bag 14. FIG. 22 illustrates the collection bag 14 comprising a hydrochromic ink/dye or a thermochromic ink/dye 93.

Where the word 'or' appears this is to be construed to mean 'and/or' such that items referred to are not necessarily mutually exclusive and may be used in any appropriate combination.

Evidence of Efficacy

A 7-day Phase 1 user trial of the device according to the present invention was undertaken in November 2021. A 28-day Phase 2 trial with a further 80 users is in progress. Details of the Phase 1 trial are as follows:

Design: Prospective cohort study. Testing and use of samples of the device by trial participants over seven days. Feedback was obtained via an online participant questionnaire.

Objectives: To determine the usability and efficacy of the device by a representative cohort of target users, in particular those with impaired physical mobility and manual dexterity, who suffer from one or more of nocturia, frequency, urgency, or post-partum urinary continence issues. More particularly, the trial was designed to identify the extent to which the device according to the present invention provides females and impaired users with an easy-to-use means of urinating unaided in challenging orientations, for example, seated on a soft surface.

Participants: 9 non-pregnant females and 3 males between 40 and 87 years old, including 2 wheelchair and walking frame users, 1 user with the use of only one hand, 1 multiple sclerosis sufferer, 3 users with osteoarthritis in the hands, and 1 user with postpartum urinary incontinence. Three users were over 75 years old, 4 were 55-64 years old, 3 were aged 45-54 and 2 were 35-44 years old.

Key outcome measures: Percentage of users who: were able to attach and detach the collection bag easily (double and single-handed); found the device easy to hold; found it easy to place in the correct position and to use; remained dry, in standing and seated orientations; believe device provides users with an ad hoc ability to urinate without third party help; were satisfied with the usability of the device.

Results: Percentage of responses:

| | % of users who Strongly agree/Agree | |
|---|---|---|
| Easy to attach & detach collection bag | 100% | |
| Easy to attach/detach collection bag single-handed | 92% | 8% Neither Agree nor Disagree |
| Easy to hold device | 100% | |
| Easy to place device in correct position | 100% | |

-continued

| | % of users who Strongly agree/Agree | |
|---|---|---|
| Easy to use - standing | 100% | |
| Easy to use - seated | 80% | 20% Neither Difficult nor Easy |
| Remained dry - standing | 100% | |
| Remained dry - seated | 80% | 20% Slightly wet on occasions |
| Easy to clean post-use | 100% | |
| Enables urination without help | 92% | 8% Neither Agree nor Disagree |
| Overall satisfaction with usability of device | 75% Very satisfied | 25% Satisfied |

Conclusions: The device meets its intended purpose of providing females and users with impaired physical mobility and manual dexterity with the ability to urinate unaided in a range of orientations notably—when seated, while remaining dry throughout.

The present invention is also described in the following clauses:

1. A blank for forming a collar adapted to support a neck portion of a collection bag, the blank comprising:
   a first portion;
   a second portion configured to be folded over to overlie the first portion;
   a fold line located between the first and second portion, wherein, when the second portion overlies the first portion, and the fold line is compressed, an aperture is defined between the first and second portions.
2. The blank of clause 1, wherein the fold line comprises a through cut that passes through the depth of the blank, wherein the through cut expands in a direction perpendicular to the fold line as the fold line is compressed, to define the aperture.
3. The blank of clause 2, wherein the fold line comprises a frangible portion, the frangible portion forming the through cut as the fold line is compressed, optionally wherein the frangible portion is a perforated line.
4. The blank of any previous clause wherein the first portion comprises a first panel and a second panel, and the second portion comprises a first panel and a second panel, wherein when the second portion overlies the first portion, the second panel of the second portion is configured to be folded to overlie the first panel of the second portion.
5. The blank of clause 4, wherein an underside of the first panel of the first portion and an underside of the first panel of the second portion are configured to engage an internal surface of the neck portion of the bag.
6. The blank of clause 4 or clause 5, wherein an underside of the second panel of the first portion and an underside of the second panel of the second portion are configured to engage an external surface of the neck portion of the bag.
7. The blank of any of clauses 4 to 6, further comprising first and second side tabs configured to extend between the first portion and the second portion when the collar is formed.
8. The blank of clause 7, wherein the first and second side tabs project from the first panel of the first portion and are configured to locate between the first and second panels of the second portion.
9. The blank of clause 8, wherein the first and second side tabs are configured to be fixed to the second panel of the second portion, optionally wherein the first and second side tabs are fixed to an underside of the second panel of the second portion.
10. The blank of any previous clause, wherein the first portion and second portion each have a tapered section adjacent the fold line, wherein the first and second portion each have a reducing width relative to the remainder of the first and second portions, wherein the width is a minimum at the fold line.
11. The blank of any of clauses 4 to 9, wherein the first panel of the first portion has a greater width than the second panel of the first portion.
12. The blank of clause 4, wherein the first and second portions each have at least one cut-out portion, optionally wherein the first panel of the first portion has a cut-out portion and the second panel of the first portion has a cut-out portion that is a mirror image of the cut-out portion of the first panel of the first portion and/or wherein the first panel of the second portion has a cut-out portion and the second panel of the second portion has a cut-out portion that is a mirror image of the cut-out portion of the first panel of the second portion.
13. The blank of clause 4, wherein a fold line is defined between the first panel and the second panel of the first portion and a fold line is defined between the first panel and the second panel of the second portion, optionally wherein each fold comprises an elliptical-shaped cut-out to define a curved top surface when the first panel of the first portion overlies the second panel of the first portion and the first panel of the second portion overlies the second panel of the second portion.
14. A method of assembling a collar adapted to support a neck portion of a collection bag, the method comprising:
   providing a blank, the blank comprising:
      a first portion;
      a second portion configured to be folded over to overlie the first portion;
      a fold line located between the first and second portion, and
   folding the second portion to overlie the first portion.
15. The method according to clause 14, wherein when the fold line is compressed, an aperture is defined between the first and second portions.

The present invention may be embodied in other specific forms without departing from the scope or spirit of the essential attributes thereof; therefore, the illustrated embodiment should be considered in all respects as illustrative and not restrictive, reference being made to the appended claims rather than to the foregoing description to indicate the scope of the invention.

The invention claimed is:

1. A liquid capture device for bodily excreta comprising:
a collection bag, comprising a collar portion and a bag portion; and
a holder adapted to support the collection bag in use;
wherein the holder has an opening, and wherein the collar portion of the collection bag is adapted to conform to the holder, and the bag portion of the collection bag is adapted to receive and store fluid, wherein the collection bag is removably attached to the holder;
wherein the attachment means comprises at least two protrusions on an external surface of opposite sides of the holder and at least two complementary cut-outs in opposite sides of the collar of the collection bag and wherein the at least two protrusions comprise a horizontal upper face and two side faces;

wherein the at least two protrusions further comprise recesses adapted to securely attach and retain the collection bag in place;

wherein the collar of the collection bag comprises a pliable material; and wherein the collection bag is configured to be attached to and released from the holder by applying light pressure to ends of the collar of the collection bag to cause slight deformation of the collar of the collection bag, said slight deformation causing the at least two complementary cut-outs of the collar to move into and out of engagement with the at least two protrusions of the holder.

2. The liquid capture device according to claim 1, further comprising an insert adapted to fix to the holder.

3. The liquid capture device according to claim 2, wherein the insert is shaped such that it conforms to the human pubic region or to human genitalia and when in use creates a seal with the human pubic region and/or human genitalia, or human anal region.

4. The liquid capture device according to claim 1, wherein the collection bag is further removably attached to the holder by one or more complementary male and female snaps on the holder and the neck of the collection bag; one or more complementary hook and eye fasteners on the holder and the neck of the collection bag; one or more toggles on the holder and one or more complementary cut outs in the neck of the collection bag; complementary hook and loop tape on the holder and the neck of the collection bag; one or more complementary magnetic strips on the holder and on the neck of the collection bag; one or more adhesive strips on the holder and/or neck of the collection bag; or combinations thereof.

5. The liquid capture device according to claim 1, wherein the collection bag further contains an absorbent material, such as one or more superabsorbent polymers or superabsorbent fibers.

6. The liquid capture device according to claim 5, wherein two different superabsorbent polymers are either attached or applied to or embodied to the inside of the collection bag, and wherein the two different superabsorbent polymers comprise a first polymer attached or applied to or embodied to an upper region of the collection bag and a second polymer attached or applied to or embodied to a bottom part of the collection bag.

7. The liquid capture device according to claim 5, wherein the absorbent material is one or more superabsorbent polymers.

8. The liquid capture device according to claim 5, wherein the absorbent material is attached or applied to or embodied within the material forming the inside of the collection bag.

9. The liquid capture device according to claim 1, wherein the collection bag further comprises at least one of a thermochromic ink and/or dye and/or a hydrochromic ink and/or dye.

10. The liquid capture device according to claim 1, wherein the collection bag further comprises a hydrochromic ink.

11. The liquid capture device according to claim 1, wherein the slight deformation of the collar causes the at least two complementary cut-outs to simultaneously move into and out of engagement with the at least two protrusions.

12. The liquid capture device according to claim 1, wherein application of the light pressure to the ends of the collar causes a single deformation of the collar that controls engagement and disengagement of each of the at least two complementary cut-outs with a respective one of the at least two protrusions.

13. The liquid capture device according to claim 1, wherein the at least two complementary cut-outs are moved into and out of engagement with the at least two protrusions in response to the applied pressure to the ends of the collar without requiring individual manipulation of the cut-outs relative to the protrusions.

14. The liquid capture device according to claim 1, wherein the slight deformation of the collar occurs as a whole and causes the at least two complementary cut-outs to move together into and out of engagement with the at least two protrusions.

15. The liquid capture device according to claim 1 wherein the light pressure applied to the ends of the collar causes the ends of the collar to be pressed inwardly towards one another to cause the slight deformation of the collar.

16. A liquid capture device comprising:

a collection bag comprising a collar;

a holder having at least two protrusions on an external surface thereof, the at least two protrusions being configured to engage the collar;

wherein the collar comprises at least two cut-outs, each of the at least two cut-outs being configured to receive a respective one of the at least two protrusions;

wherein the collar comprises a pliable material; and wherein the collection bag is configured to be attached to and released from the holder by applying pressure to ends of the collar to cause deformation of the collar, the deformation of the collar enabling each of the at least two cut-outs to move into and out of engagement with the respective one of the at least two protrusions.

17. The liquid capture device according to claim 15, wherein the deformation of the collar enables the at least two cut-outs to simultaneously move into and out of engagement with the respective one of the at least two protrusions in response to the applied pressure.

* * * * *